United States Patent
Takiguchi et al.

(10) Patent No.: US 7,976,958 B2
(45) Date of Patent: Jul. 12, 2011

(54) METAL COMPLEX COMPOUND, ELECTROLUMINESCENT DEVICE AND DISPLAY APPARATUS

(75) Inventors: Takao Takiguchi, Chofu (JP); Masashi Hashimoto, Tokyo (JP); Jun Kamatani, Tokyo (JP); Satoshi Igawa, Fujisawa (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 896 days.

(21) Appl. No.: 11/945,581

(22) Filed: Nov. 27, 2007

(65) Prior Publication Data

US 2008/0131730 A1 Jun. 5, 2008

(30) Foreign Application Priority Data

Nov. 28, 2006 (JP) .................. 2006-320083

(51) Int. Cl.
H01L 51/54 (2006.01)
C09K 11/06 (2006.01)

(52) U.S. Cl. .......... 428/690; 428/917; 313/504; 257/40; 257/E51.044

(58) Field of Classification Search .......... None
See application file for complete search history.

(56) References Cited

U.S. PATENT DOCUMENTS

| | | | |
|---|---|---|---|
| 6,812,497 B2 | 11/2004 | Kamatani et al. | |
| 6,815,091 B2 | 11/2004 | Takiguchi et al. | |
| 6,824,894 B2 | 11/2004 | Takiguchi et al. | |
| 6,838,818 B2 | 1/2005 | Furugori et al. | |
| 7,026,062 B2 | 4/2006 | Takiguchi et al. | |
| 7,078,115 B2 | 7/2006 | Takiguchi et al. | |
| 7,108,924 B2 | 9/2006 | Kamatani et al. | |
| 7,166,958 B2 | 1/2007 | Furugori et al. | |
| 7,189,466 B2 | 3/2007 | Moriyama et al. | |
| 2002/0034656 A1* | 3/2002 | Thompson et al. | 428/690 |
| 2003/0224208 A1* | 12/2003 | Kamatani et al. | 428/690 |
| 2005/0084710 A1 | 4/2005 | Kishino et al. | |
| 2005/0276994 A1 | 12/2005 | Iwawaki et al. | |
| 2006/0066225 A1 | 3/2006 | Kishino et al. | |
| 2006/0280968 A1 | 12/2006 | Kamatani et al. | |
| 2007/0085473 A1 | 4/2007 | Moriyama et al. | |
| 2007/0207344 A1 | 9/2007 | Kamatani et al. | |
| 2007/0228940 A1 | 10/2007 | Hashimoto et al. | |
| 2007/0231600 A1 | 10/2007 | Kamatani et al. | |
| 2007/0232803 A1 | 10/2007 | Kamatani et al. | |
| 2007/0259207 A1 | 11/2007 | Hashimoto et al. | |
| 2007/0278939 A1 | 12/2007 | Tsuboyama et al. | |

FOREIGN PATENT DOCUMENTS

JP 2003146996 5/2003

* cited by examiner

*Primary Examiner* — Marie R. Yamnitzky
(74) *Attorney, Agent, or Firm* — Fitzpatrick, Cella, Harper & Scinto

(57) ABSTRACT

A novel metal complex compound for an organic EL device is provided which has at least one partial structure represented by the general formula (1):

M1L1   (1)

in which the partial structure M1L1 is represented by the general formula (2):

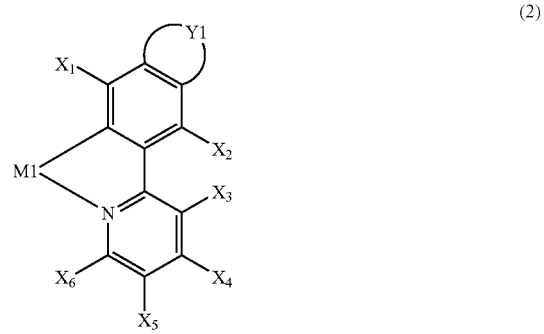

wherein M1 represents a metal atom selected from Ir, Pt, Rh, and Pd; $Y_1$ represents an alkylene group having 2 to 6 carbon atoms; and at least one of hydrogen atoms directly bonded to the carbon atoms forming the alkylene group $Y_1$ is substituted with a fluorine atom.

9 Claims, 3 Drawing Sheets

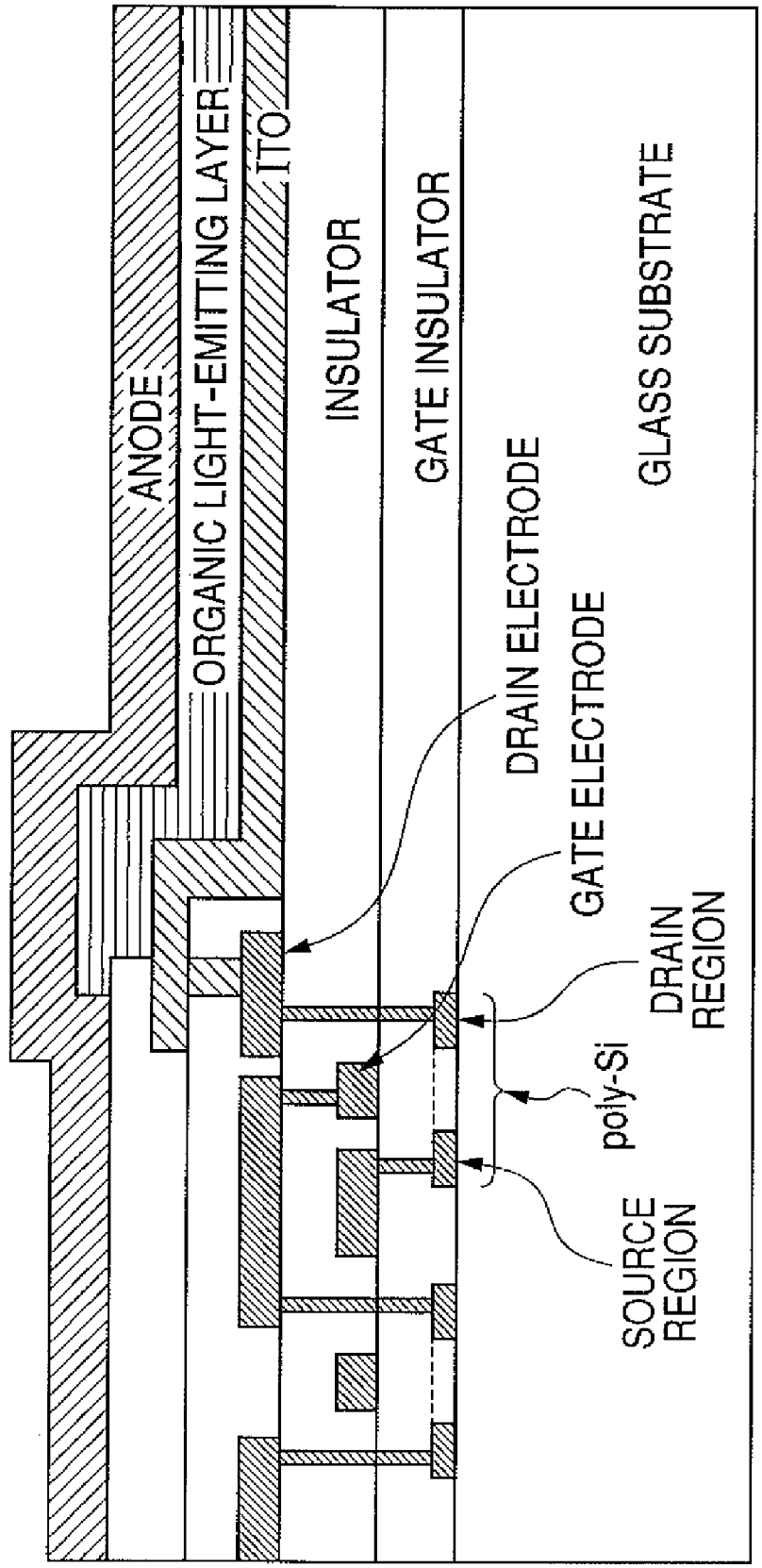

METAL COMPLEX COMPOUND, ELECTROLUMINESCENT DEVICE AND DISPLAY APPARATUS

BACKGROUND OF THE INVENTION

1. Field of the Invention

The present invention relates to a novel metal complex compound for a light-emitting device and an organic electroluminescent device (hereinafter, sometimes referred to as "organic EL device") for use in, for example, a surface light source or a flat panel display.

2. Description of the Related Art

Recent progress of an organic light-emitting device is remarkable. The organic light-emitting device has high responsibility, a small thickness, and a light weight, can be driven at a low applied voltage, and provides a high luminance and a variety of emission wavelengths, which suggests applicability to a wide variety of uses.

However, at present, an optical output of a higher luminance and a higher conversion efficiency are required. In addition, there still remain a large number of problems in terms of durability such as a change over time during long-term use and degradation due to an atmospheric gas containing oxygen or to moisture. Furthermore, light emission of blue, green and red colors having a high color purity is necessary when application to a full-color display or the like is attempted. However, those problems have not been sufficiently solved yet.

In addition, a large number of aromatic compounds and condensed polycyclic aromatic compounds have been studied as fluorescent organic compounds used for an electron-transporting layer, a light-emitting layer, and the like. However, it is difficult to say that a compound sufficiently satisfying the emission luminance and durability requirements has been already obtained.

Japanese Patent Application Laid-Open No. 2003-146996 discloses applying to an organic EL device a metal complex compound related to the metal complex compound of the present invention. However, there is no disclosure in this patent document of the below-mentioned metal complex compound of the present invention having the partial structure represented by general formula (2) below in which at least one of hydrogen atoms directly bonded to carbon atoms forming the alkylene group $Y_1$ is substituted with a fluorine atom.

SUMMARY OF THE INVENTION

The present invention provides a novel metal complex compound for an organic EL device and an organic light-emitting device using the compound, having an optical output with high efficiency and high luminance. The present invention also provides an organic light-emitting device having high durability. Further, the present invention provides an organic light-emitting device that can easily be produced at a relatively low cost.

That is, according to the present invention, there is provided a metal complex compound having at least one partial structure represented by the following general formula (1):

$$M1L1 \tag{1}$$

in which the partial structure M1L1 is represented by the following general formula (2):

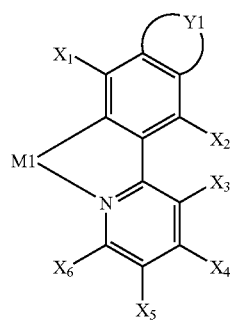

(2)

wherein M1 represents a metal atom selected from Ir, Pt, Rh, and Pd; $Y_1$ represents an alkylene group having 2 to 6 carbon atoms in which one methylene group or two non-adjacent methylene groups of the alkylene group may be replaced by —O—, —S—, or —CO—, a hydrogen atom of the alkylene group may be substituted with a linear or branched alkyl group having 1 to 10 carbon atoms, and a hydrogen atom of the alkyl group may be substituted with a fluorine atom; $X_1$, $X_2$, $X_3$, $X_4$, $X_5$, and $X_6$ each represent, independently of one another, a hydrogen atom, a halogen atom, a cyano group, a nitro group, a disubstituted amino group, a trialkylsilyl group, or a linear or branched alkyl group having 1 to 20 carbon atoms; the substituents of the disubstituted amino group each represent, independently of one another, a substituted or unsubstituted aromatic ring group in which a CH forming the ring may be replaced by N, or a linear or branched alkyl group having 1 to 8 carbon atoms in which a hydrogen atom of the alkyl group may be substituted with a fluorine atom; the alkyl groups of the trialkylsilyl group each represent, independently of one another, a linear or branched alkyl group having 1 to 8 carbon atoms; one methylene group or at least two non-adjacent methylene groups of the linear or branched alkyl group having 1 to 20 carbon atoms may each be replaced by —O—, —S—, —CO—, —CO—O—, —O—CO—, —CH═CH—, or —C≡C—, one methylene group or at least two methylene groups of the alkyl group may each be replaced by a substituted or unsubstituted divalent aromatic ring group, a hydrogen atom of the alkyl group may be substituted with a fluorine atom, and a substituent of the divalent aromatic ring group is selected from a halogen atom, a cyano group, a nitro group, a trialkylsilyl group in which the alkyl groups of the trialkylsilyl group are each independently a linear or branched alkyl group having 1 to 8 carbon atoms, and a linear or branched alkyl group having 1 to 20 carbon atoms in which one methylene group or at least two non-adjacent methylene groups may each be replaced by —O—, —S—, —CO—, —CO—O—, —O—CO—, —CH═CH—, or —C≡C—, and a hydrogen atom of the alkyl group may be substituted with a fluorine atom; and adjacent ones of $X_3$, $X_4$, $X_5$, and $X_6$ may be joined to form a ring, provided that at least one of hydrogen atoms directly bonded to the carbon atoms forming the alkylene group $Y_1$ is substituted with a fluorine atom.

As described above, a light-emitting device using the metal complex compound of the present invention is an excellent device capable of emitting light with high efficiency. In addition, the light-emitting device of the present invention can be an excellent display device.

Further features of the present invention will become apparent from the following description of exemplary embodiments with reference to the attached drawings.

BRIEF DESCRIPTION OF THE DRAWINGS

FIG. 4 is a schematic view illustrating an example of a sectional structure of a TFT substrate.

DESCRIPTION OF THE EMBODIMENTS

Figure 1A:
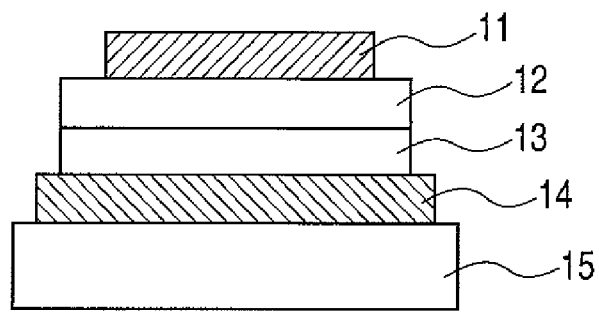
FIGS. 1A, 1B and 1C are views each illustrating an example of a light-emitting device of the present invention.

First, the metal complex compound of the present invention will be described.

The compound of the present invention has a partial structure represented by the general formula (2) in which at least one of hydrogen atoms directly bonded to the carbon atoms which form the alkylene group $Y_1$ is substituted with a fluorine atom. The case where at least two of the hydrogen atoms directly bonded to the carbon atoms forming the alkylene group $Y_1$ are each substituted with a fluorine atom is preferable, and the case where at least four of the hydrogen atoms are each substituted with a fluorine atom is more preferable. The case where all the hydrogen atoms are each substituted with a fluorine atom is also preferable.

The introduction of a fluorine atom into the molecule is expected to exert an effect of suppressing the intermolecular interaction. As a result, a phenomenon (referred to as concentration quenching) that the emission efficiency is reduced with increasing concentration of a guest material in a host material, which is frequently observed in a light-emitting layer of an organic electroluminescent device and poses a problem when a Guest-Host type light-emitting layer is formed, can be suppressed. Accordingly, the concentration at which a light-emitting material is dispersed in a host material can be increased, and hence a light-emitting device containing the light-emitting material at a high concentration and having high emission efficiency can be obtained.

Further, a light-emitting device having a light-emitting layer which is not a Guest-Host type mixture layer but is formed only of the compound of the present invention being a guest material (that is, the content of the compound is 100%) can also be provided.

In addition, by reducing the intermolecular interaction, the sublimation temperature is reduced, so that the decomposition during vacuum vapor deposition is prevented, and the compound can be stably formed into a film by vapor deposition. Further, sublimation purification is easily applicable to the purification of the compound.

The metal complex compound of the present invention exhibits phosphorescence, and its lowest excited state is considered to be a Metal-to-Ligand charge transfer (MLCT*) excited state or a $\pi$-$\pi$* excited state each serving as a triplet state. Phosphorescence occurs upon transition from each of those states to a ground state.

The phosphorescence lifetime obtained by a light emission experiment on photoluminescence caused by the photoexcitation of Exemplified Compound No. 76 to be described later was 0.26 µsec. A short phosphorescence lifetime is a condition for an improvement in emission efficiency when used for an EL device. That is, a long phosphorescence lifetime has involved the problem that the number of molecules existing in a triplet excited state to emit light increases and the emission efficiency is reduced particularly at a high current density. The material of the present invention is a material suitable as a light-emitting material for an EL device having a high phosphorescence yield and a short phosphorescence lifetime.

In addition, the adjustment of the emission wavelength can be expected by changing the structure of the alkylene group $Y_1$ or the substituent $X_1$ or $X_2$, and the emission wavelength can be reduced by substituting at lease one of hydrogen atoms directly bonded to the carbon atoms which form the alkylene group $Y_1$ with a fluorine atom. Also from the foregoing viewpoint, the metal complex compound of the present invention is suitable as a light-emitting material for an EL device.

In the general formula (1), M1 preferably represents Ir or Pt, or more preferably represents Ir.

In the general formula (2), $Y_1$ is preferably selected from groups of A to D"" shown below (at least one of $R_1$ to $R_{12}$ of each of the groups represents a fluorine atom), or is more preferably selected from A to T and M' to I". In addition, the case where at least two of $R_1$ to $R_{12}$ of each of A to D"" each represent a fluorine atom is preferable, and the case where at least four of $R_1$ to $R_{12}$ of each of A to D"" each represent a fluorine atom is more preferable. The case where all of $R_1$ to $R_{12}$ of each of A to D"" each represent a fluorine atom is also preferable.

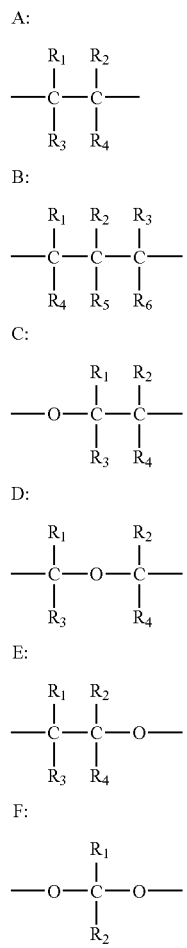

G:
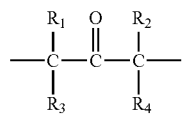
H:
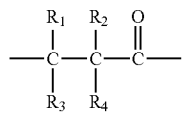
I:
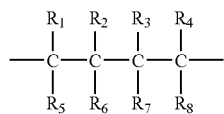
J:
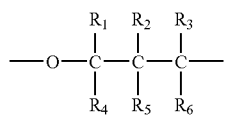
K:
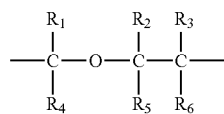
L:
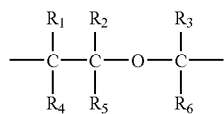
M:
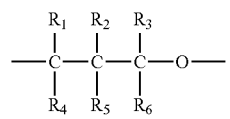
N:
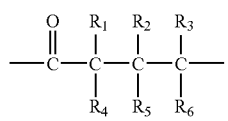
O:
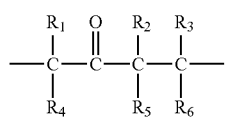
P:
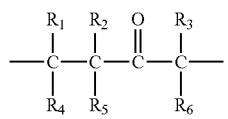
Q:
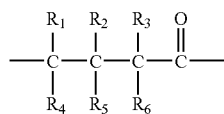
R:
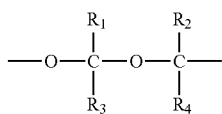
S:
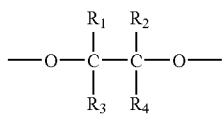
T:
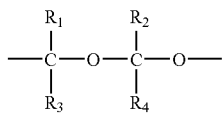
U:
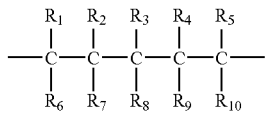
V:
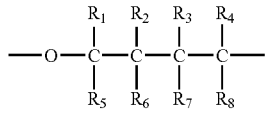
W:
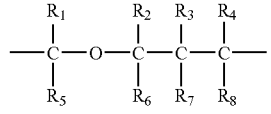
X:
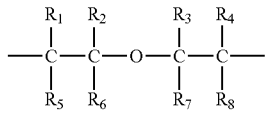
Y:
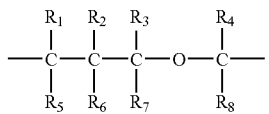
Z:
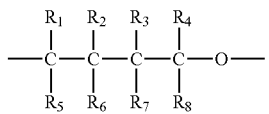
A':
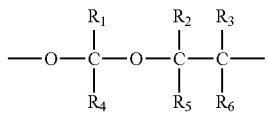
B':
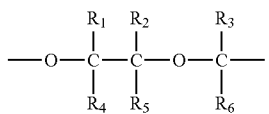

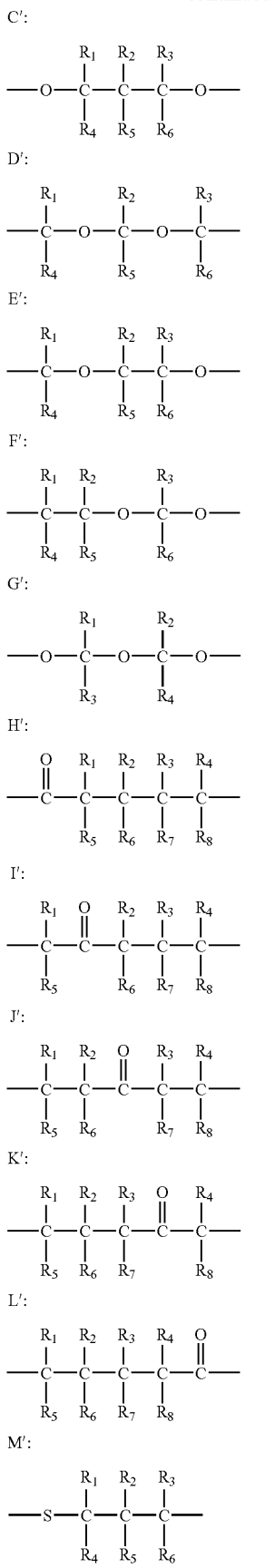
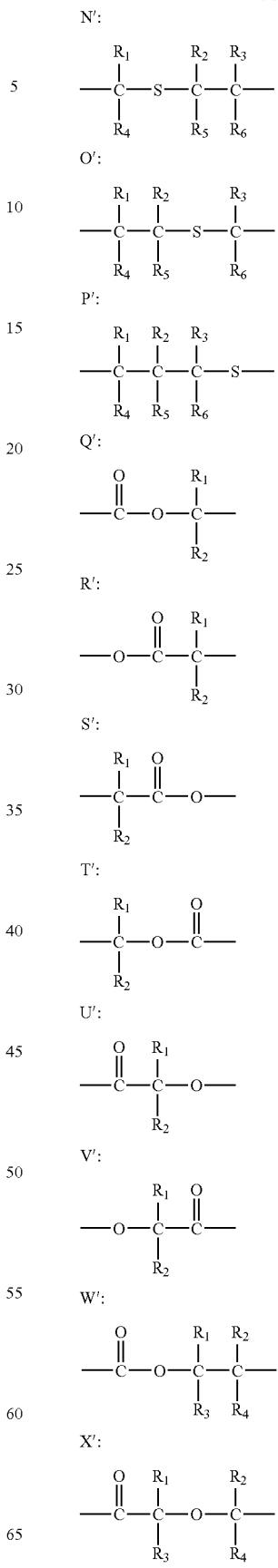

Y′:
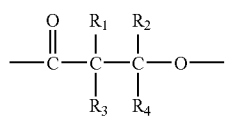
Z′:
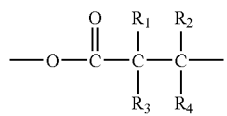
A″:
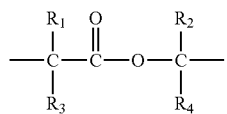
B″:
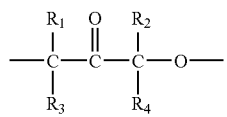
C″:
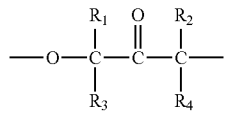
D″:
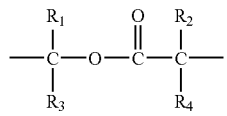
E″:
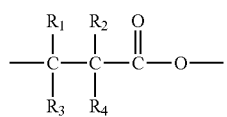
F″:
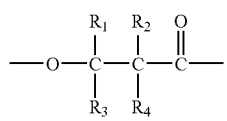
G″:
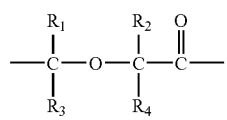
H″:
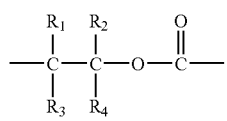
I″:
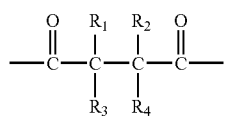
J″:
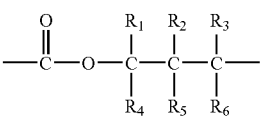
K″:
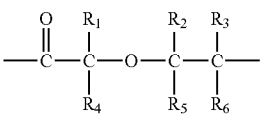
L″:
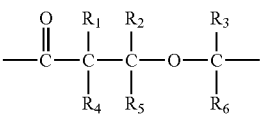
M″:
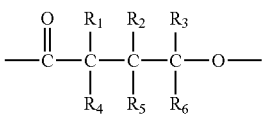
N″:
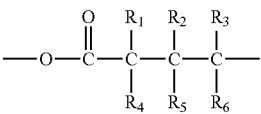
O″:
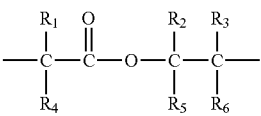
P″:
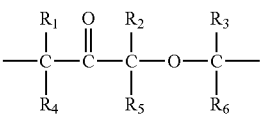
Q″:
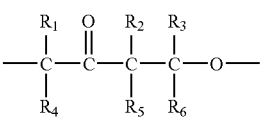
R″:
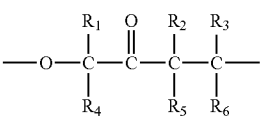
S″:
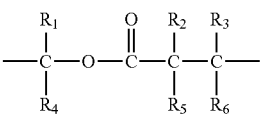
T″:
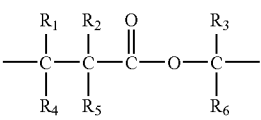

U″:
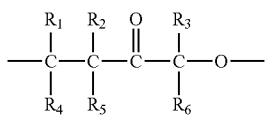
V″:
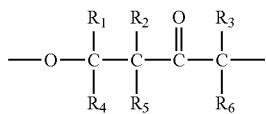
W″:
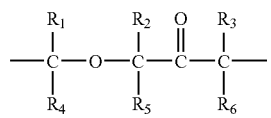
X″:
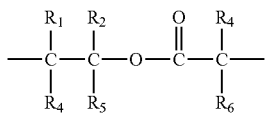
Y″:
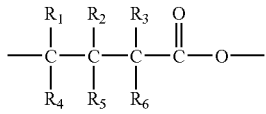
Z″:
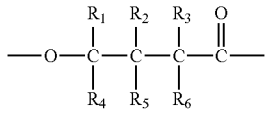
A‴:
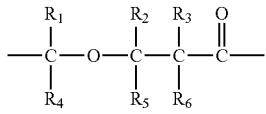
B‴:
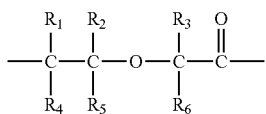
C‴:
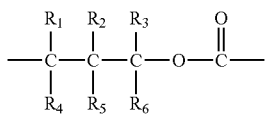
D‴:
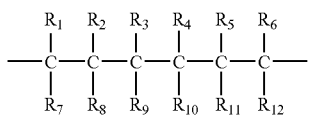
E‴:
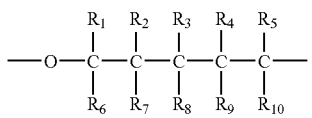
F‴:
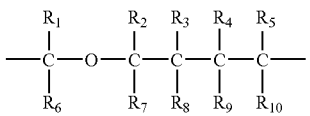
G‴:
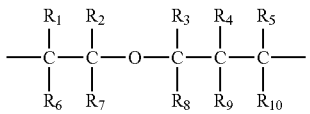
H‴:
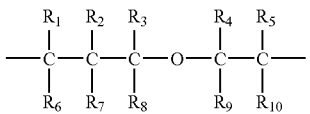
I‴:
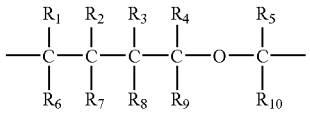
J‴:
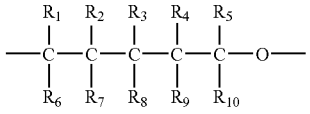
K‴:
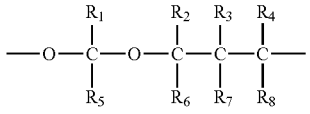
L‴:
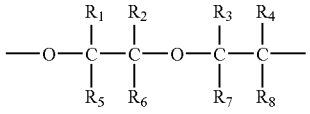
M‴:
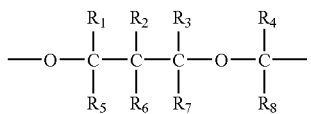
N‴:
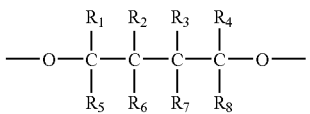
O‴:
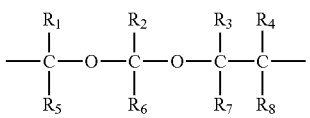
P‴:
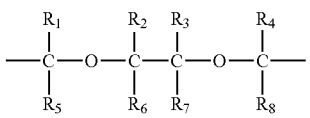

Q''':
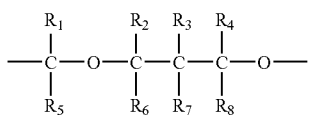

R''':
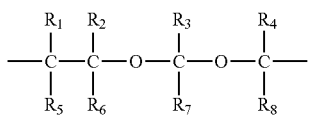

S''':
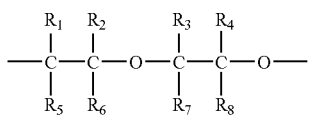

T''':
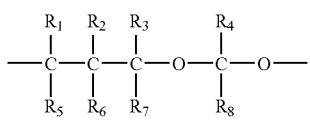

U''':
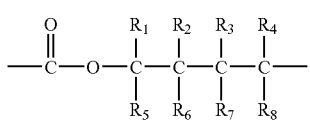

V''':
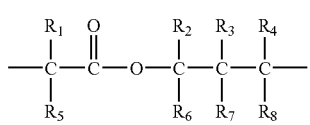

W''':
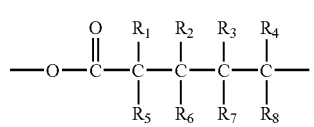

X''':
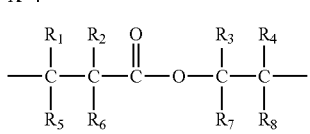

Y''':
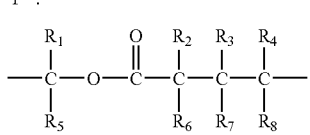

Z''':
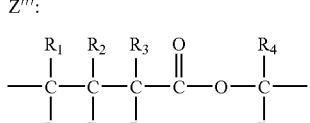

A'''':
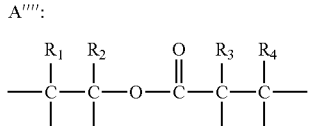

B'''':
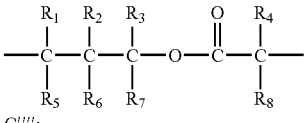

C'''':
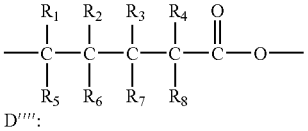

D'''':
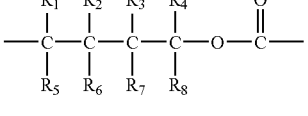

It is preferable that $X_1$ and $X_2$ be each independently selected from a hydrogen atom, a halogen atom, and a linear or branched alkyl group having 1 to 20 carbon atoms (one methylene group or at least two non-adjacent methylene groups of the alkyl group may each be replaced by —O—, and hydrogen atom(s) of the alkyl group may be substituted with fluorine atom(s)).

It is more preferable that $X_1$ and $X_2$ be each independently selected from a hydrogen atom, a halogen atom, a trifluoromethyl group, a trifluoromethoxy group, and a linear or branched alkyl group having 1 to 4 carbon atoms (hydrogen atom(s) of the alkyl group may be substituted with fluorine atom(s)). It is still more preferable that $X_1$ and $X_2$ be each independently selected from a hydrogen atom, a fluorine atom, a methyl group, a trifluoromethyl group, and a trifluoromethoxy group.

It is preferable that $X_3$, $X_4$, $X_5$, and $X_6$ be each independently selected from the following groups, and adjacent ones of $X_3$, $X_4$, $X_5$, and $X_6$ can be joined to form a ring: a hydrogen atom, a halogen atom, a linear or branched alkyl group having 1 to 20 carbon atoms (one methylene group or at least two non-adjacent methylene groups of the alkyl group may each be replaced by —O—, and hydrogen atom(s) of the alkyl group may be substituted with fluorine atom(s)), and a disubstituted amino group (the substituents of the disubstituted amino group are each independently a substituted or unsubstituted aromatic ring group (in which CH forming the ring may be replaced with N), or a linear or branched alkyl group having 1 to 8 carbon atoms (hydrogen atom(s) of the alkyl group may be substituted with fluorine atom(s)).

Further, it is more preferable that $X_3$, $X_4$, $X_5$, and $X_6$ be each independently selected from the following groups: a hydrogen atom, a halogen atom, a trifluoromethyl group, a trifluoromethoxy group, a linear or branched alkyl group having 1 to 4 carbon atoms (hydrogen atom(s) of the alkyl group may be substituted with fluorine atom(s)), a linear or branched alkoxy group having 1 to 4 carbon atoms (hydrogen atom(s) of the alkyl group may be substituted with fluorine atom(s)), a dialkylamino group (the alkyl groups of the dialkylamino group are each independently selected from a methyl group, an ethyl group, a propyl group, an isopropyl group, and a butyl group), a diphenylamino group, and a naphthylphenylamino group.

Moreover, it is still more preferable that $X_3$, $X_4$, $X_5$, and $X_6$ be each independently selected from the following groups: a hydrogen atom, a fluorine atom, a methyl group, a trifluoromethyl group, a trifluoromethoxy group, a methoxy group, a linear or branched alkyl group having 2 to 4 carbon atoms, a linear or branched alkoxy group having 2 to 4 carbon atoms, a dimethylamino group, a diethylamino group, and a diphenylamino group.

A compound represented by the following general formula (3) is preferably used as the metal complex compound of the present invention:

$$M1L1_mL1'_n \quad (3)$$

wherein L1 and L1' represent different bidentate ligands; m represents 1, 2, or 3, and n represents 0, 1, or 2, provided that m+n represents 2 or 3.

The partial structure $M1L1'_n$ is represented by the following general formula (4), (5), or (6):

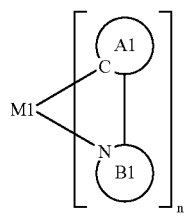

(4)

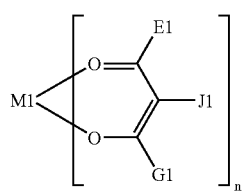

(5)

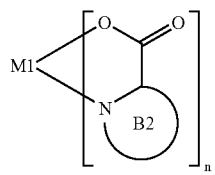

(6)

In the formulae (4), (5), and (6), N and C represent a nitrogen atom and a carbon atom, respectively, A1 represents a substituted or unsubstituted cyclic group which contains the carbon atom and is bonded to a metal atom M1 through the carbon atom, B1 and B2 each represent a substituted or unsubstituted cyclic group which contains the nitrogen atom and is bonded to the metal atom M1 through the nitrogen atom, and the cyclic group A1 and the cyclic group B1 are covalently bonded The substituents of the cyclic groups A1, B1, and B2 are each independently selected from a halogen atom, a cyano group, a nitro group, a disubstituted amino group, a trialkylsilyl group, and a linear or branched alkyl group having 1 to 20 carbon atoms.

The substituents of the disubstituted amino group are each independently a substituted or unsubstituted aromatic ring group (in which CH forming the ring may be replaced with N), or a linear or branched alkyl group having 1 to 8 carbon atoms (hydrogen atom(s) of the alkyl group may be substituted with fluorine atom).

The alkyl groups of the trialkylsilyl group are each independently a linear or branched alkyl group having 1 to 8 carbon atoms.

Further, one methylene group or at least two non-adjacent methylene groups of the linear or branched alkyl group having 1 to 20 carbon atoms may each be replaced by —O—, —S—, —CO—, —CO—O—, —O—CO—, —CH=CH—, or —C≡C—, one methylene group or at least two methylene groups may be replaced by a substituted or unsubstituted divalent aromatic ring group, and hydrogen atom(s) of the alkyl group may be substituted with fluorine atom(s). The substituent of the divalent aromatic ring group is selected from a halogen atom, a cyano group, a nitro group, a trialkylsilyl group (the alkyl groups are each independently a linear or branched alkyl group having 1 to 8 carbon atoms), and a linear or branched alkyl group having 1 to 20 carbon atoms (one methylene group or at least two non-adjacent methylene groups of the alkyl group may each be replaced by —O—, —S—, —CO—, —CO—O—, —O—CO—, —CH=CH—, or —C≡C—, and hydrogen atom(s) of the alkyl group may be substituted with fluorine atom(s)).

E1 and G1 are each independently selected from a linear or branched alkyl group having 1 to 20 carbon atoms, and a substituted or unsubstituted aromatic ring group, and J1 is selected from a hydrogen atom, a linear or branched alkyl group having 1 to 20 carbon atoms, and a substituted or unsubstituted aromatic ring group.

One methylene group or at least two non-adjacent methylene groups of the linear or branched alkyl group having 1 to 20 carbon atoms may each be replaced by —O—, —S—, —CO—, —CO—O—, —O—CO—, —CH=CH—, or —C≡C—, one methylene group or at least two methylene groups may each be replaced by a substituted or unsubstituted divalent aromatic ring group, and hydrogen atom(s) of the alkyl group may be substituted with fluorine atom(s). The substituent of the divalent aromatic ring group is selected from a halogen atom, a cyano group, a nitro group, a trialkylsilyl group (the alkyl groups are each independently a linear or branched alkyl group having 1 to 8 carbon atoms), and a linear or branched alkyl group having 1 to 20 carbon atoms (one methylene group or at least two non-adjacent methylene groups of the alkyl group may each be replaced by —O—, —S—, —CO—, —CO—O—, —O—CO—, —CH=CH—, or —C≡C—, and hydrogen atom(s) of the alkyl group may be substituted with a fluorine atom(s)).

The substituent of the aromatic ring group is selected from a halogen atom, a cyano group, a nitro group, a trialkylsilyl group (the alkyl groups are each independently a linear or branched alkyl group having 1 to 8 carbon atoms), and a linear or branched alkyl group having 1 to 20 carbon atoms (one methylene group or at least two non-adjacent methylene groups of the alkyl group may be replaced by —O—, —S—, —CO—, —CO—O—, —O—CO—, —CH=CH—, or —C≡C—, and hydrogen atom(s) of the alkyl group may be substituted with fluorine atom(s)).

In the general formula (3), m is preferably 2 or 3, and n is preferably 0 or 1.

The cyclic group A1 is preferably a phenyl group, a naphthyl group, a fluorenyl group, a thienyl group, a quinolinyl group, a cinnolinyl group, a benzothienyl group, or a benzofuranyl group, more preferably a phenyl group, a naphthyl group, a fluorenyl group, a thienyl group, a quinolinyl group, or a cinnolinyl group, and still more preferably a phenyl group or a naphthyl group.

Preferable examples of the ring structures B1 and B2 include a pyridyl group, a pyrazinyl group, a pyrimidyl group, a pyridazinyl group, a triazinyl group, a quinolinyl group, an isoquinolinyl group, a phenanthridinyl group, an acridinyl group, a naphthyridinyl group, a quinoxalinyl group, a quinazolinyl group, a cinnolinyl group, a phthalazinyl group, a phenanthrolyl group, a thiazolyl group, an isothiazolyl group, an imidazolyl group, a pyrazolyl group, an oxazolyl group, an isoxazolyl group, a benzothiazolyl group, a benzisothiazolyl group, a benzimidazolyl group, a benzopyrazolyl group, a benzoxazolyl group, a benzoisoxazolyl group, an imidazolinyl group, a pyrazolinyl group, and an oxazolinyl group.

Further, more preferable examples thereof include a pyridyl group, a pyrazinyl group, a pyrimidyl group, a pyridazinyl group, a triazinyl group, a quinolinyl group, an isoquinolinyl group, a quinoxalinyl group, a phenanthrolyl group, a thiazolyl group, an isothiazolyl group, an imidazolyl group, a pyrazolyl group, an oxazolyl group, and an isoxazolyl group.

Further, still more preferable examples thereof include a pyridyl group, a pyrimidyl group, and a pyridazinyl group.

Preferable examples of the substituent of the cyclic groups A1, B1, and B2 include a halogen atom, a linear or branched alkyl group, a linear or branched alkyl group substituted with fluorine atom(s), a linear or branched alkoxyl group substituted with fluorine atom(s), a dialkylamino group, and a diphenylamino group. More preferable examples of the substituent of the cyclic groups include a fluorine atom, a methyl group, an ethyl group, a trifluoromethyl group, a trifluoromethoxy group, a methoxy group, an ethoxy group, a dimethylamino group, and a diphenylamino group.

E1 and G1 each preferably represent any one of a methyl group, a tertiary-butyl group, a trifluoromethyl group, a methoxy group, an ethoxy group, and a phenyl group, and more preferably represent any one of a methyl group, a tertiary-butyl group, a methoxy group, and a phenyl group.

J1 preferably represents a hydrogen atom, a methyl group, a tertiary-butyl group, a trifluoromethyl group, a methoxy group, an ethoxy group, and a phenyl group, and more preferably represents one of a hydrogen atom, a methyl group, a methoxy group, and a phenyl group.

A synthesis route of a metal complex compound of the present invention will be shown below by taking an iridium coordination compound as an example.

Synthesis of Ligand L1

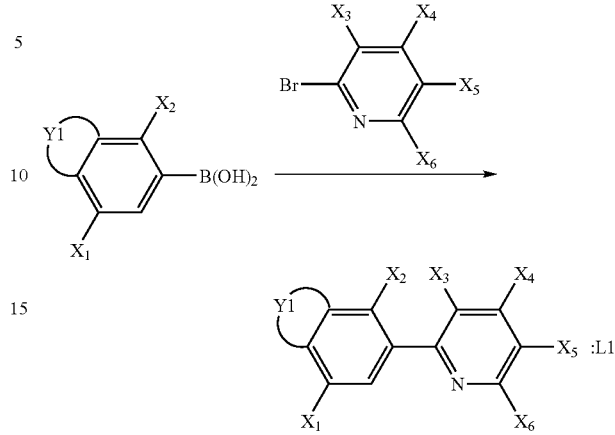

Synthesis of Iridium Coordination Compound

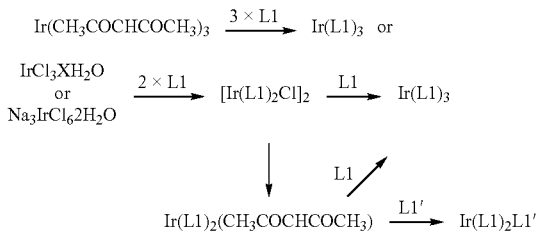

Hereinafter, specific structural formulae of the metal coordination compound of the present invention will be shown. However, these formulae are mere representative examples, and the present invention is not limited thereto.

Incidentally, in the following tables, A to D'''' used in the column of $Y_1$, respectively, correspond to those described for $Y_1$ of the general formula (2) above, and Ph1 to N2p used in the columns A1, B1, B2, E1, G1, and J1, respectively, represent the following structures.

TABLE 1

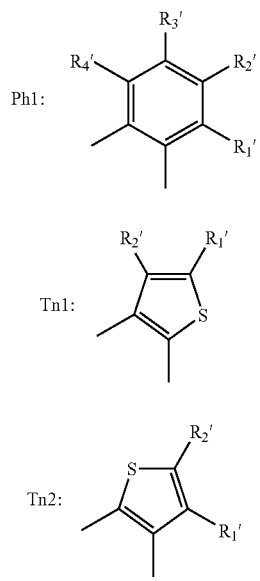

Np1: 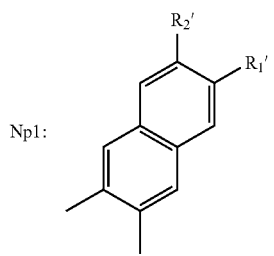
Np2: 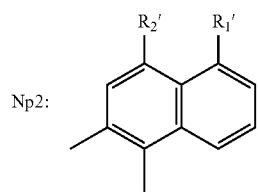
Cn1: 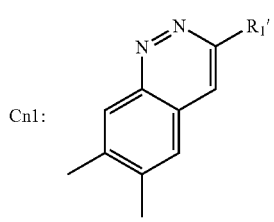
Cn2: 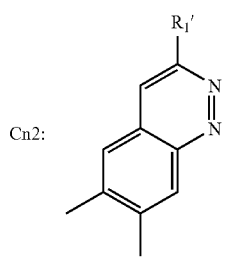
Qn1: 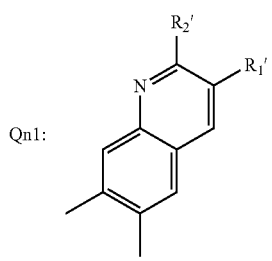
Qn2: 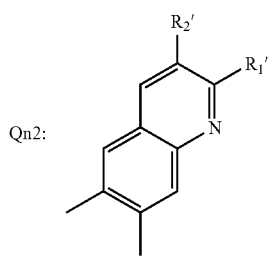
Pi: 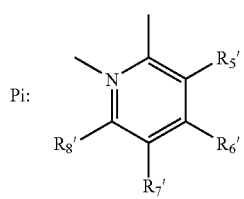

Pr: 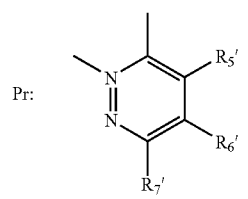
Py1: 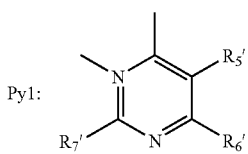
Py2: 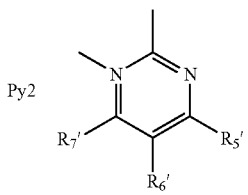
Ph: 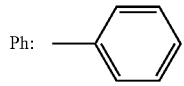
N1p: 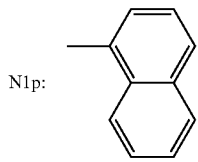
N2p: 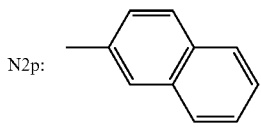
| | | | | L1 | | | | | | | | | |
|---|---|---|---|---|---|---|---|---|---|---|---|---|---|
| | | | | Y1 | | | | | | | | | |
| No | M | m | n | R1 R5 R9 | R2 R6 R10 | R3 R7 R11 | R4 R8 R12 | X1 | X2 | X3 | X4 | X5 | X6 |
| 1 | Ir | 3 | 0 | A | | | | H | H | H | H | H | H |
| | | | | F | H | H | H | | | | | | |
| | | | | — | — | — | — | | | | | | |
| 2 | Ir | 3 | 0 | A | | | | H | F | H | CH3 | H | H |
| | | | | F | F | H | H | | | | | | |
| | | | | — | — | — | — | | | | | | |
| 3 | Ir | 3 | 0 | A | | | | H | H | H | OCH3 | H | H |
| | | | | F | F | F | H | | | | | | |
| | | | | — | — | — | — | | | | | | |
| 4 | Ir | 3 | 0 | A | | | | H | H | H | N(CH3)2 | H | H |
| | | | | F | F | F | F | | | | | | |
| | | | | — | — | — | — | | | | | | |
| 5 | Ir | 3 | 0 | A | | | | H | H | H | H | H | H |
| | | | | F | F | F | F | | | | | | |
| | | | | — | — | — | — | | | | | | |

| No | M | m | n | Y1 (R1 R2 R3 R4 / R5 R6 R7 R8 / R9 R10 R11 R12) | X1 | X2 | X3 | X4 | X5 | X6 |
|---|---|---|---|---|---|---|---|---|---|---|
| 6 | Ir | 3 | 0 | A | H | H | H | OCH3 | H | H |
| 7 | Ir | 3 | 0 | B (F F F F / — — — — / — — — —) | H | H | H | H | H | H |
| 8 | Ir | 3 | 0 | B (F H H F / H H — — / — — — —) | F | H | H | C2H5 | H | H |
| 9 | Ir | 3 | 0 | B (H H F H / H F — — / — — — —) | H | H | H | OC4H9 | H | H |
| 10 | Ir | 3 | 0 | B (F H F F / H F — — / — — — —) | H | H | H | N(CH3)2 | H | H |
| 11 | Ir | 3 | 0 | B (F F F F / F F — — / — — — —) | H | H | H | H | H | H |
| 12 | Ir | 3 | 0 | C (F F F F / F F — — / — — — —) | H | H | H | N(Ph)2 | H | H |
| 13 | Ir | 3 | 0 | C (F H F H / — — — — / — — — —) | CF3 | H | H | H | H | H |
| 14 | Ir | 3 | 0 | C (H F H F / — — — — / — — — —) | H | H | H | OCH3 | H | H |
| 15 | Ir | 3 | 0 | C (F F F F / — — — — / — — — —) | H | H | H | H | H | H |

TABLE 2

| No | M | m | n | Y1 (R1 R2 R3 R4 / R5 R6 R7 R8 / R9 R10 R11 R12) | X1 | X2 | X3 | X4 | X5 | X6 |
|---|---|---|---|---|---|---|---|---|---|---|
| 16 | Ir | 3 | 0 | D (F H F H / — — — — / — — — —) | H | H | H | H | H | H |
| 17 | Ir | 3 | 0 | D (H F H F / — — — — / — — — —) | H | H | H | OCH3 | H | H |
| 18 | Ir | 3 | 0 | D (F F F F / — — — — / — — — —) | H | H | H | H | H | H |

TABLE 2-continued

| No | M | m | n | Y1: R1, R2, R3, R4 / R5, R6, R7, R8 / R9, R10, R11, R12 | X1 | X2 | X3 | X4 | X5 | X6 |
|---|---|---|---|---|---|---|---|---|---|---|
| 19 | Ir | 3 | 0 | D; F F F F / — — — — / — — — — | H | H | H | N(C2H5)2 | H | H |
| 20 | Ir | 3 | 0 | E; F H F H / — — — — / — — — — | OCF3 | H | H | H | H | H |
| 21 | Ir | 3 | 0 | E; H F H F / — — — — / — — — — | H | H | H | N(CH3)Ph | H | H |
| 22 | Ir | 3 | 0 | E; F F F F / — — — — / — — — — | H | H | H | OC3H7 | H | H |
| 23 | Ir | 3 | 0 | E; F F F F / — — — — / — — — — | H | H | H | H | H | H |
| 24 | Ir | 3 | 0 | F; F F — — / — — — — / — — — — | H | H | H | H | H | H |
| 25 | Ir | 3 | 0 | G; F F F F / — — — — / — — — — | H | F | H | H | H | H |
| 26 | Ir | 3 | 0 | H; F F F F / — — — — / — — — — | H | H | H | OCH3 | H | H |
| 27 | Ir | 3 | 0 | I; F H H H / H H H H / — — — — | H | OCF3 | H | H | H | H |
| 28 | Ir | 3 | 0 | I; F H H H / F H H H / — — — — | H | CF3 | H | H | H | H |
| 29 | Ir | 3 | 0 | I; H F H H / H F H H / — — — — | H | H | H | OCH3 | H | H |
| 30 | Ir | 3 | 0 | I; H H F H / H H F H / — — — — | H | H | H | H | H | H |

TABLE 3

| | | | | L1 | | | | | | | | | |
|---|---|---|---|---|---|---|---|---|---|---|---|---|---|
| | | | | Y1 | | | | | | | | | |
| No | M | m | n | R1 R5 R9 | R2 R6 R10 | R3 R7 R11 | R4 R8 R12 | X1 | X2 | X3 | X4 | X5 | X6 |
| 31 | Ir | 3 | 0 | | I | | | H | H | H | N(N1p)Ph | H | H |
| | | | | H H — | H H — | H H — | F F — | | | | | | |
| 32 | Ir | 3 | 0 | | I | | | H | H | H | H | H | H |
| | | | | F F — | H H — | H H — | F F — | | | | | | |
| 33 | Ir | 3 | 0 | | I | | | H | H | H | OCH3 | H | H |
| | | | | F F — | H H — | H H — | F F — | | | | | | |
| 34 | Ir | 3 | 0 | | I | | | H | H | H | N(CH3)2 | H | H |
| | | | | F F — | H H — | H H — | F F — | | | | | | |
| 35 | Ir | 3 | 0 | | I | | | H | H | H | H | N(Ph)2 | H |
| | | | | F F — | H H — | H H — | F F — | | | | | | |
| 36 | Ir | 3 | 0 | | I | | | H | H | H | N(CH3)Ph | H | H |
| | | | | F F — | H H — | H H — | F F — | | | | | | |
| 37 | Ir | 3 | 0 | | I | | | H | H | H | N(N1p)Ph | H | H |
| | | | | F F — | H H — | H H — | F F — | | | | | | |
| 38 | Ir | 3 | 0 | | I | | | CH3 | H | H | CH3 | H | H |
| | | | | F F — | H H — | H H — | F F — | | | | | | |
| 39 | Ir | 3 | 0 | | I | | | H | H | H | C2H5 | H | H |
| | | | | F F — | H H — | H H — | F F — | | | | | | |
| 40 | Ir | 3 | 0 | | I | | | H | H | H | N(N2p)Ph | H | H |
| | | | | F F — | H H — | H H — | F F — | | | | | | |
| 41 | Ir | 3 | 0 | | I | | | H | H | H | H | H | CH3 |
| | | | | F F — | H H — | H H — | F F — | | | | | | |
| 42 | Ir | 3 | 0 | | I | | | H | H | H | OC2H5 | H | H |
| | | | | F F — | H H — | H H — | F F — | | | | | | |
| 43 | Ir | 3 | 0 | | I | | | H | H | H | H | N(C3H7)2 | H |
| | | | | F F — | H H — | H H — | F F — | | | | | | |
| 44 | Ir | 3 | 0 | | I | | | H | H | H | H | H | H |
| | | | | F F — | F F — | F F — | F F — | | | | | | |

TABLE 3-continued

| No | M | m | n | L1 / Y1 / R1 R2 R3 R4 / R5 R6 R7 R8 / R9 R10 R11 R12 | X1 | X2 | X3 | X4 | X5 | X6 |
|---|---|---|---|---|---|---|---|---|---|---|
| 45 | Ir | 3 | 0 | I<br>F F F F<br>F F F F<br>— — — — | H | H | H | OCH3 | H | H |

TABLE 4

| No | M | m | n | L1 / Y1 / R1 R2 R3 R4 / R5 R6 R7 R8 / R9 R10 R11 R12 | X1 | X2 | X3 | X4 | X5 | X6 |
|---|---|---|---|---|---|---|---|---|---|---|
| 46 | Ir | 3 | 0 | J<br>F H H F<br>H H — —<br>— — — — | H | H | H | H | H | H |
| 47 | Ir | 3 | 0 | J<br>H H F H<br>H F — —<br>— — — — | H | H | H | H | OCH3 | H |
| 48 | Ir | 3 | 0 | J<br>F H F F<br>H F — —<br>— — — — | H | H | H | N(CH3)Ph | H | H |
| 49 | Ir | 3 | 0 | J<br>F F F F<br>F F — —<br>— — — — | H | H | H | H | H | H |
| 50 | Ir | 3 | 0 | J<br>F F F F<br>F F — —<br>— — — — | H | H | H | OCH3 | H | H |
| 51 | Ir | 3 | 0 | K<br>F H H F<br>H H — —<br>— — — — | H | H | H | OC5H11 | H | H |
| 52 | Ir | 3 | 0 | K<br>H H F H<br>H F — —<br>— — — — | H | H | H | H | H | H |
| 53 | Ir | 3 | 0 | K<br>F H F F<br>H F — —<br>— — — — | H | H | H | N(C3H7)2 | H | H |
| 54 | Ir | 3 | 0 | K<br>F F F F<br>F F — —<br>— — — — | H | H | H | H | H | H |
| 55 | Ir | 3 | 0 | K<br>F F F F<br>F F — —<br>— — — — | H | H | H | OCH3 | H | H |

TABLE 4-continued

| No | M | m | n | Y1 | R1/R5/R9 | R2/R6/R10 | R3/R7/R11 | R4/R8/R12 | X1 | X2 | X3 | X4 | X5 | X6 |
|----|---|---|---|----|----------|-----------|-----------|-----------|----|----|----|-----|----|----|
| 56 | Ir | 3 | 0 | L | F / H / — | H / H / — | H / — / — | F / — / — | H | H | H | H | H | H |
| 57 | Ir | 3 | 0 | L | H / H / — | H / F / — | F / — / — | H / — / — | H | H | H | OCH3 | H | H |
| 58 | Ir | 3 | 0 | L | F / H / — | H / F / — | F / — / — | F / — / — | H | H | H | H | H | H |
| 59 | Ir | 3 | 0 | L | F / F / — | F / F / — | F / — / — | F / — / — | H | H | H | N(N2p)Ph | H | H |
| 60 | Ir | 3 | 0 | L | F / F / — | F / F / — | F / — / — | F / — / — | H | H | H | H | H | H |

TABLE 5

| No | M | m | n | Y1 | R1/R5/R9 | R2/R6/R10 | R3/R7/R11 | R4/R8/R12 | X1 | X2 | X3 | X4 | X5 | X6 |
|----|---|---|---|----|----------|-----------|-----------|-----------|----|----|----|-----|----|----|
| 61 | Ir | 3 | 0 | M | F / H / — | H / H / — | H / — / — | F / — / — | H | H | H | H | H | H |
| 62 | Ir | 3 | 0 | M | H / H / — | H / F / — | F / — / — | H / — / — | H | H | H | OCH3 | H | H |
| 63 | Ir | 3 | 0 | M | F / H / — | H / F / — | F / — / — | F / — / — | H | H | H | H | H | H |
| 64 | Ir | 3 | 0 | M | F / F / — | F / F / — | F / — / — | F / — / — | H | H | H | N(C3H7)2 | H | H |
| 65 | Ir | 3 | 0 | N | F / H / — | H / H / — | H / — / — | F / — / — | H | H | H | OCH3 | H | H |
| 66 | Ir | 3 | 0 | N | H / H / — | H / F / — | F / — / — | H / — / — | H | H | H | H | H | H |

TABLE 5-continued

| No | M | m | n | Y1 | R1 R5 R9 | R2 R6 R10 | R3 R7 R11 | R4 R8 R12 | X1 | X2 | X3 | X4 | X5 | X6 |
|---|---|---|---|---|---|---|---|---|---|---|---|---|---|---|
| 67 | Ir | 3 | 0 | N | | | | | H | H | H | N(N1p)Ph | H | H |
| | | | | | F | F | F | F | | | | | | |
| | | | | | F | F | — | — | | | | | | |
| | | | | | — | — | — | — | | | | | | |
| 68 | Ir | 3 | 0 | O | | | | | H | H | H | H | H | H |
| | | | | | H | H | F | H | | | | | | |
| | | | | | H | F | — | — | | | | | | |
| | | | | | — | — | — | — | | | | | | |
| 69 | Ir | 3 | 0 | O | | | | | H | H | H | OCH3 | H | H |
| | | | | | F | F | F | F | | | | | | |
| | | | | | F | F | — | — | | | | | | |
| | | | | | — | — | — | — | | | | | | |
| 70 | Ir | 3 | 0 | P | | | | | H | H | H | N(CH3)Ph | H | H |
| | | | | | F | H | F | F | | | | | | |
| | | | | | H | F | — | — | | | | | | |
| | | | | | — | — | — | — | | | | | | |
| 71 | Ir | 3 | 0 | P | | | | | H | H | H | H | H | H |
| | | | | | F | F | F | F | | | | | | |
| | | | | | F | F | — | — | | | | | | |
| | | | | | — | — | — | — | | | | | | |
| 72 | Ir | 3 | 0 | Q | | | | | H | H | H | OCH3 | H | H |
| | | | | | H | H | F | H | | | | | | |
| | | | | | H | F | — | — | | | | | | |
| | | | | | — | — | — | — | | | | | | |
| 73 | Ir | 3 | 0 | Q | | | | | H | H | H | H | H | H |
| | | | | | F | F | F | F | | | | | | |
| | | | | | F | F | — | — | | | | | | |
| | | | | | — | — | — | — | | | | | | |
| 74 | Ir | 3 | 0 | R | | | | | H | H | H | H | H | H |
| | | | | | F | H | F | H | | | | | | |
| | | | | | — | — | — | — | | | | | | |
| | | | | | — | — | — | — | | | | | | |
| 75 | Ir | 3 | 0 | R | | | | | H | H | H | OCH3 | H | H |
| | | | | | H | F | H | F | | | | | | |
| | | | | | — | — | — | — | | | | | | |
| | | | | | — | — | — | — | | | | | | |

TABLE 6

| No | M | m | n | Y1 | R1 R5 R9 | R2 R6 R10 | R3 R7 R11 | R4 R8 R12 | X1 | X2 | X3 | X4 | X5 | X6 |
|---|---|---|---|---|---|---|---|---|---|---|---|---|---|---|
| 76 | Ir | 3 | 0 | R | | | | | H | H | H | H | H | H |
| | | | | | F | F | F | F | | | | | | |
| | | | | | — | — | — | — | | | | | | |
| | | | | | — | — | — | — | | | | | | |
| 77 | Ir | 3 | 0 | R | | | | | H | H | H | OCH3 | H | H |
| | | | | | F | F | F | F | | | | | | |
| | | | | | — | — | — | — | | | | | | |
| | | | | | — | — | — | — | | | | | | |

TABLE 6-continued

| | | | | L1 | | | | | | | | | |
|---|---|---|---|---|---|---|---|---|---|---|---|---|---|
| | | | | Y1 | | | | | | | | | |
| No | M | m | n | R1 R5 R9 | R2 R6 R10 | R3 R7 R11 | R4 R8 R12 | X1 | X2 | X3 | X4 | X5 | X6 |
| 78 | Ir | 3 | 0 | — — F | — — F | R — — F | — — F | H | H | H | OC6H13 | H | H |
| 79 | Ir | 3 | 0 | — — F | — — F | R — — F | — — F | H | H | H | N(CH3)2 | H | H |
| 80 | Ir | 3 | 0 | — — F | — — F | R — — F | — — F | H | H | H | N(CH3)Ph | H | H |
| 81 | Ir | 3 | 0 | — — F | — — F | R — — F | — — F | H | H | H | N(C3H7)2 | H | H |
| 82 | Ir | 3 | 0 | — — F | — — F | R — — F | — — F | H | H | H | N(N2p)Ph | H | H |
| 83 | Ir | 3 | 0 | — — F | — — F | R — — F | — — F | H | H | H | N(Ph)2 | H | H |
| 84 | Ir | 3 | 0 | — — F | — — F | R — — F | — — F | H | H | H | CH3 | H | H |
| 85 | Ir | 3 | 0 | — — F | — — F | R — — F | — — F | H | H | H | C4H9 | H | H |
| 86 | Ir | 3 | 0 | — — F | — — H | S — — F | — — H | H | H | H | CH3 | H | H |
| 87 | Ir | 3 | 0 | — — H | — — F | S — — H | — — F | H | H | H | N(CH3)2 | H | H |
| 88 | Ir | 3 | 0 | — — F | — — F | S — — F | — — F | H | H | H | H | H | H |
| 89 | Ir | 3 | 0 | — — F | — — F | S — — F | — — F | H | H | H | CH3 | H | H |
| 90 | Ir | 3 | 0 | — — F | — — F | S — — F | — — F | H | H | H | OCH3 | H | H |

TABLE 7

| No | M | m | n | Y1 (R1 R2 R3 R4 / R5 R6 R7 R8 / R9 R10 R11 R12) | X1 | X2 | X3 | X4 | X5 | X6 |
|---|---|---|---|---|---|---|---|---|---|---|
| 91 | Ir | 3 | 0 | S | H | H | H | N(CH3)2 | H | H |
|    |    |   |   | F F F F / — — — — / — — — — |    |    |    |    |    |    |
| 92 | Ir | 3 | 0 | S | H | H | H | N(Ph)2 | H | H |
|    |    |   |   | F F F F / — — — — / — — — — |    |    |    |    |    |    |
| 93 | Ir | 3 | 0 | T | H | F | H | H | H | H |
|    |    |   |   | F H F H / — — — — / — — — — |    |    |    |    |    |    |
| 94 | Ir | 3 | 0 | T | H | H | H | H | H | H |
|    |    |   |   | H F H F / — — — — / — — — — |    |    |    |    |    |    |
| 95 | Ir | 3 | 0 | T | H | H | H | H | H | H |
|    |    |   |   | F F F F / — — — — / — — — — |    |    |    |    |    |    |
| 96 | Ir | 3 | 0 | T | H | H | H | OC2H5 | H | H |
|    |    |   |   | F F F F / — — — — / — — — — |    |    |    |    |    |    |
| 97 | Ir | 3 | 0 | U | H | H | H | H | H | H |
|    |    |   |   | F F F F / F F F F / F F — — |    |    |    |    |    |    |
| 98 | Ir | 3 | 0 | V | H | H | H | H | CH3 | H |
|    |    |   |   | F F F F / F F F F / — — — — |    |    |    |    |    |    |
| 99 | Ir | 3 | 0 | W | H | H | H | H | H | H |
|    |    |   |   | F F F F / F F F F / — — — — |    |    |    |    |    |    |
| 100 | Ir | 3 | 0 | X | H | H | H | H | H | OCH3 |
|    |    |   |   | F F F F / F F F F / — — — — |    |    |    |    |    |    |
| 101 | Ir | 3 | 0 | Y | H | H | H | H | H | H |
|    |    |   |   | F F F F / F F F F / — — — — |    |    |    |    |    |    |
| 102 | Ir | 3 | 0 | Z | H | H | H | N(CH3)2 | H | H |
|    |    |   |   | F F F F / F F F F / — — — — |    |    |    |    |    |    |
| 103 | Ir | 3 | 0 | A' | H | H | H | OC2H5 | H | H |
|    |    |   |   | F F F F / F F — — / — — — — |    |    |    |    |    |    |
| 104 | Ir | 3 | 0 | B' | H | H | H | H | H | H |
|    |    |   |   | F F F F / F F — — / — — — — |    |    |    |    |    |    |

TABLE 7-continued

| | | | | L1 | | | | | | | | |
| | | | | Y1 | | | | | | | | |
| No | M | m | n | R1, R2, R3, R4 / R5, R6, R7, R8 / R9, R10, R11, R12 | | | | X1 | X2 | X3 | X4 | X5 | X6 |
|---|---|---|---|---|---|---|---|---|---|---|---|---|---|
| 105 | Ir | 3 | 0 | | C' | | | H | H | H | H | H | H |
| | | | | F | F | F | F | | | | | | |
| | | | | F | F | — | — | | | | | | |
| | | | | — | — | — | — | | | | | | |

TABLE 8

| | | | | L1 | | | | | | | | |
| | | | | Y1 | | | | | | | | |
| No | M | m | n | R1, R2, R3, R4 / R5, R6, R7, R8 / R9, R10, R11, R12 | | | | X1 | X2 | X3 | X4 | X5 | X6 |
|---|---|---|---|---|---|---|---|---|---|---|---|---|---|
| 106 | Ir | 3 | 0 | | D' | | | H | H | H | CH3 | H | H |
| | | | | F | F | F | F | | | | | | |
| | | | | F | F | — | — | | | | | | |
| | | | | — | — | — | — | | | | | | |
| 107 | Ir | 3 | 0 | | E' | | | H | H | H | H | H | H |
| | | | | F | F | F | F | | | | | | |
| | | | | F | F | — | — | | | | | | |
| | | | | — | — | — | — | | | | | | |
| 108 | Ir | 3 | 0 | | F' | | | H | H | H | N(CH3)2 | H | H |
| | | | | F | F | F | F | | | | | | |
| | | | | F | F | — | — | | | | | | |
| | | | | — | — | — | — | | | | | | |
| 109 | Ir | 3 | 0 | | G' | | | H | H | H | H | H | H |
| | | | | F | F | F | F | | | | | | |
| | | | | — | — | — | — | | | | | | |
| | | | | — | — | — | — | | | | | | |
| 110 | Pt | 2 | 0 | | H' | | | H | H | H | N(Ph)2 | H | H |
| | | | | F | F | F | F | | | | | | |
| | | | | F | F | F | F | | | | | | |
| | | | | — | — | — | — | | | | | | |
| 111 | Ir | 3 | 0 | | I' | | | H | H | H | H | H | H |
| | | | | F | F | F | F | | | | | | |
| | | | | F | F | F | F | | | | | | |
| | | | | — | — | — | — | | | | | | |
| 112 | Ir | 3 | 0 | | J' | | | H | H | H | N(C3H7)2 | H | H |
| | | | | F | F | F | F | | | | | | |
| | | | | F | F | F | F | | | | | | |
| | | | | — | — | — | — | | | | | | |
| 113 | Rh | 3 | 0 | | K' | | | H | H | H | H | H | H |
| | | | | F | F | F | F | | | | | | |
| | | | | F | F | F | F | | | | | | |
| | | | | — | — | — | — | | | | | | |
| 114 | Ir | 3 | 0 | | L' | | | H | H | H | H | OC2H5 | H |
| | | | | F | F | F | F | | | | | | |
| | | | | F | F | F | F | | | | | | |
| | | | | — | — | — | — | | | | | | |
| 115 | Ir | 3 | 0 | | M' | | | H | H | H | H | H | H |
| | | | | F | F | F | F | | | | | | |
| | | | | F | F | — | — | | | | | | |
| | | | | — | — | — | — | | | | | | |

TABLE 8-continued

| No | M | m | n | R1 R5 R9 | R2 R6 R10 | R3 R7 R11 | R4 R8 R12 | X1 | X2 | X3 | X4 | X5 | X6 |
|---|---|---|---|---|---|---|---|---|---|---|---|---|---|
| 116 | Ir | 3 | 0 | \<L1, Y1 = N'\> | | | | Cl | H | H | H | H | H |
|  |  |  |  | F | F | F | F |  |  |  |  |  |  |
|  |  |  |  | F | F | — | — |  |  |  |  |  |  |
|  |  |  |  | — | — | — | — |  |  |  |  |  |  |
| 117 | Ir | 3 | 0 | \<L1, Y1 = O'\> | | | | H | H | H | CH3 | H | H |
|  |  |  |  | F | F | F | F |  |  |  |  |  |  |
|  |  |  |  | F | F | — | — |  |  |  |  |  |  |
|  |  |  |  | — | — | — | — |  |  |  |  |  |  |
| 118 | Ir | 3 | 0 | \<L1, Y1 = P'\> | | | | H | H | H | OCH3 | H | H |
|  |  |  |  | F | F | F | F |  |  |  |  |  |  |
|  |  |  |  | F | F | — | — |  |  |  |  |  |  |
|  |  |  |  | — | — | — | — |  |  |  |  |  |  |
| 119 | Ir | 3 | 0 | \<L1, Y1 = Q'\> | | | | H | H | H | H | H | H |
|  |  |  |  | F | F | — | — |  |  |  |  |  |  |
|  |  |  |  | — | — | — | — |  |  |  |  |  |  |
|  |  |  |  | — | — | — | — |  |  |  |  |  |  |
| 120 | Ir | 3 | 0 | \<L1, Y1 = R'\> | | | | H | H | H | OC2H5 | H | H |
|  |  |  |  | F | F | — | — |  |  |  |  |  |  |
|  |  |  |  | — | — | — | — |  |  |  |  |  |  |
|  |  |  |  | — | — | — | — |  |  |  |  |  |  |

TABLE 9

| No | M | m | n | R1 R5 R9 | R2 R6 R10 | R3 R7 R11 | R4 R8 R12 | X1 | X2 | X3 | X4 | X5 | X6 |
|---|---|---|---|---|---|---|---|---|---|---|---|---|---|
| 121 | Pd | 2 | 0 | \<L1, Y1 = S'\> | | | | H | H | H | H | H | H |
|  |  |  |  | F | F | — | — |  |  |  |  |  |  |
|  |  |  |  | — | — | — | — |  |  |  |  |  |  |
|  |  |  |  | — | — | — | — |  |  |  |  |  |  |
| 122 | Ir | 3 | 0 | \<L1, Y1 = T'\> | | | | H | H | H | N(CH3)2 | H | H |
|  |  |  |  | F | F | — | — |  |  |  |  |  |  |
|  |  |  |  | — | — | — | — |  |  |  |  |  |  |
|  |  |  |  | — | — | — | — |  |  |  |  |  |  |
| 123 | Ir | 3 | 0 | \<L1, Y1 = U'\> | | | | H | H | H | H | H | H |
|  |  |  |  | F | F | — | — |  |  |  |  |  |  |
|  |  |  |  | — | — | — | — |  |  |  |  |  |  |
|  |  |  |  | — | — | — | — |  |  |  |  |  |  |
| 124 | Ir | 3 | 0 | \<L1, Y1 = V'\> | | | | H | H | H | H | H | H |
|  |  |  |  | F | F | — | — |  |  |  |  |  |  |
|  |  |  |  | — | — | — | — |  |  |  |  |  |  |
|  |  |  |  | — | — | — | — |  |  |  |  |  |  |
| 125 | Rh | 3 | 0 | \<L1, Y1 = W'\> | | | | H | H | H | N(Ph)2 | H | H |
|  |  |  |  | F | F | F | F |  |  |  |  |  |  |
|  |  |  |  | — | — | — | — |  |  |  |  |  |  |
|  |  |  |  | — | — | — | — |  |  |  |  |  |  |
| 126 | Ir | 3 | 0 | \<L1, Y1 = X'\> | | | | H | H | H | H | H | H |
|  |  |  |  | F | F | F | F |  |  |  |  |  |  |
|  |  |  |  | — | — | — | — |  |  |  |  |  |  |
|  |  |  |  | — | — | — | — |  |  |  |  |  |  |

TABLE 9-continued

| No | M | m | n | L1 / Y1 / R1 R5 R9 | R2 R6 R10 | R3 R7 R11 | R4 R8 R12 | X1 | X2 | X3 | X4 | X5 | X6 |
|---|---|---|---|---|---|---|---|---|---|---|---|---|---|
| 127 | Ir | 3 | 0 | Y' | | | | H | H | H | OCH3 | H | H |
| | | | | F — — | F — — | F — — | F — — | | | | | | |
| 128 | Ir | 3 | 0 | Z' | | | | H | H | H | H | H | H |
| | | | | F — — | F — — | F — — | F — — | | | | | | |
| 129 | Ir | 3 | 0 | A'' | | | | H | H | H | N(CH3)2 | H | H |
| | | | | F — — | F — — | F — — | F — — | | | | | | |
| 130 | Ir | 3 | 0 | B'' | | | | H | H | H | H | H | H |
| | | | | F — — | F — — | F — — | F — — | | | | | | |
| 131 | Pt | 2 | 0 | C'' | | | | H | H | H | N(Ph)2 | H | H |
| | | | | F — — | F — — | F — — | F — — | | | | | | |
| 132 | Ir | 3 | 0 | D'' | | | | H | H | H | H | H | H |
| | | | | F — — | F — — | F — — | F — — | | | | | | |
| 133 | Ir | 3 | 0 | E'' | | | | H | H | H | H | H | H |
| | | | | F — — | F — — | F — — | F — — | | | | | | |
| 134 | Ir | 3 | 0 | F'' | | | | H | H | H | OCH3 | H | H |
| | | | | F — — | F — — | F — — | F — — | | | | | | |
| 135 | Ir | 3 | 0 | G'' | | | | H | H | H | H | H | H |
| | | | | F — — | F — — | F — — | F — — | | | | | | |

TABLE 10

| No | M | m | n | L1 / Y1 / R1 R5 R9 | R2 R6 R10 | R3 R7 R11 | R4 R8 R12 | X1 | X2 | X3 | X4 | X5 | X6 |
|---|---|---|---|---|---|---|---|---|---|---|---|---|---|
| 136 | Ir | 3 | 0 | H'' | | | | H | H | H | H | H | H |
| | | | | F — — | F — — | F — — | F — — | | | | | | |
| 137 | Ir | 3 | 0 | I'' | | | | H | H | H | N(CH3)2 | H | H |
| | | | | F — — | F — — | F — — | F — — | | | | | | |

TABLE 10-continued

| No | M | m | n | Y1 (R1 R5 R9) | Y1 (R2 R6 R10) | Y1 (R3 R7 R11) | Y1 (R4 R8 R12) | X1 | X2 | X3 | X4 | X5 | X6 |
|---|---|---|---|---|---|---|---|---|---|---|---|---|---|
| 138 | Ir | 3 | 0 | | J" | | | H | H | H | H | H | H |
| | | | | F F — | F F — | F — — | F — — | | | | | | |
| 139 | Ir | 3 | 0 | | K" | | | H | H | H | H | H | H |
| | | | | F F — | F F — | F — — | F — — | | | | | | |
| 140 | Ir | 3 | 0 | | L" | | | H | H | H | H | H | H |
| | | | | F F — | F F — | F — — | F — — | | | | | | |
| 141 | Ir | 3 | 0 | | M" | | | H | H | H | OC2H5 | H | H |
| | | | | F F — | F F — | F — — | F — — | | | | | | |
| 142 | Ir | 3 | 0 | | N" | | | H | H | H | N(CH3)Ph | H | H |
| | | | | F F — | F F — | F — — | F — — | | | | | | |
| 143 | Pd | 2 | 0 | | Q" | | | H | H | H | H | H | H |
| | | | | F F — | F F — | F — — | F — — | | | | | | |
| 144 | Ir | 3 | 0 | | R" | | | H | H | H | H | H | H |
| | | | | F F — | F F — | F — — | F — — | | | | | | |
| 145 | Ir | 3 | 0 | | S" | | | H | H | H | OC6H13 | H | H |
| | | | | F F — | F F — | F — — | F — — | | | | | | |
| 146 | Ir | 3 | 0 | | T" | | | H | H | H | N(CH3)2 | H | H |
| | | | | F F — | F F — | F — — | F — — | | | | | | |
| 147 | Ir | 3 | 0 | | U" | | | H | H | H | H | H | H |
| | | | | F F — | F F — | F — — | F — — | | | | | | |
| 148 | Ir | 3 | 0 | | V" | | | H | H | H | H | H | H |
| | | | | F F — | F F — | F — — | F — — | | | | | | |
| 149 | Ir | 3 | 0 | | W" | | | H | H | H | OCH3 | H | OCH3 |
| | | | | F F — | F F — | F — — | F — — | | | | | | |
| 150 | Ir | 3 | 0 | | X" | | | H | CF3 | H | H | H | H |
| | | | | F F — | F F — | F — — | F — — | | | | | | |

TABLE 11

| | | | | L1 | | | | | | | | |
|---|---|---|---|---|---|---|---|---|---|---|---|---|
| | | | | Y1 | | | | | | | | |
| No | M | m | n | R1 R2 R3 R4<br>R5 R6 R7 R8<br>R9 R10 R11 R12 | | | | X1 | X2 | X3 | X4 | X5 | X6 |
| 151 | Ir | 3 | 0 | Y'' | | | | H | H | H | N(Ph)2 | H | H |
| | | | | F | F | F | F | | | | | | |
| | | | | F | F | — | — | | | | | | |
| | | | | — | — | | | | | | | | |
| 152 | Ir | 3 | 0 | Z'' | | | | H | H | H | H | H | H |
| | | | | F | F | F | F | | | | | | |
| | | | | F | F | — | — | | | | | | |
| | | | | — | — | | | | | | | | |
| 153 | Ir | 3 | 0 | A''' | | | | H | H | H | OCH3 | H | H |
| | | | | F | F | F | F | | | | | | |
| | | | | F | F | — | — | | | | | | |
| | | | | — | — | | | | | | | | |
| 154 | Rh | 3 | 0 | B''' | | | | H | H | H | H | H | H |
| | | | | F | F | F | F | | | | | | |
| | | | | F | F | — | — | | | | | | |
| | | | | — | — | | | | | | | | |
| 155 | Ir | 3 | 0 | C''' | | | | H | H | H | H | H | H |
| | | | | F | F | F | F | | | | | | |
| | | | | F | F | — | — | | | | | | |
| | | | | — | — | | | | | | | | |
| 156 | Ir | 3 | 0 | O'' | | | | H | H | H | N(CH3)Ph | H | H |
| | | | | F | F | F | F | | | | | | |
| | | | | F | F | — | — | | | | | | |
| | | | | — | — | | | | | | | | |
| 157 | Ir | 3 | 0 | B'' | | | | H | H | H | H | H | H |
| | | | | F | F | F | F | | | | | | |
| | | | | F | F | — | — | | | | | | |
| | | | | — | — | | | | | | | | |
| 158 | Ir | 3 | 0 | D''' | | | | H | H | H | H | N(CH3)2 | H |
| | | | | F | F | F | F | | | | | | |
| | | | | F | F | F | F | | | | | | |
| | | | | F | F | F | F | | | | | | |
| 159 | Ir | 3 | 0 | E''' | | | | H | H | H | N(C3H7)2 | H | H |
| | | | | F | F | F | F | | | | | | |
| | | | | F | F | F | F | | | | | | |
| | | | | F | F | — | — | | | | | | |
| 160 | Ir | 3 | 0 | E''' | | | | H | H | H | H | H | H |
| | | | | F | F | F | F | | | | | | |
| | | | | F | F | F | F | | | | | | |
| | | | | F | F | — | — | | | | | | |
| 161 | Ir | 3 | 0 | F''' | | | | H | H | H | OCH3 | H | H |
| | | | | F | F | F | F | | | | | | |
| | | | | F | F | F | F | | | | | | |
| | | | | F | F | — | — | | | | | | |
| 162 | Ir | 3 | 0 | G''' | | | | H | H | H | H | H | H |
| | | | | F | F | F | F | | | | | | |
| | | | | F | F | F | F | | | | | | |
| | | | | F | F | — | — | | | | | | |
| 163 | Ir | 3 | 0 | H''' | | | | H | H | H | OC4H9 | H | H |
| | | | | F | F | F | F | | | | | | |
| | | | | F | F | F | F | | | | | | |
| | | | | F | F | — | — | | | | | | |
| 164 | Ir | 3 | 0 | I''' | | | | H | H | H | H | H | H |
| | | | | F | F | F | F | | | | | | |
| | | | | F | F | F | F | | | | | | |
| | | | | F | F | — | — | | | | | | |

TABLE 11-continued

| No | M | m | n | L1 / Y1 / R1 R2 R3 R4 / R5 R6 R7 R8 / R9 R10 R11 R12 | | | | X1 | X2 | X3 | X4 | X5 | X6 |
|---|---|---|---|---|---|---|---|---|---|---|---|---|---|
| 165 | Ir | 3 | 0 | J''' | | | | H | H | H | N(N1p)Ph | H | H |
| | | | | F | F | F | F | | | | | | |
| | | | | F | F | F | F | | | | | | |
| | | | | F | F | — | — | | | | | | |

TABLE 12

| No | M | m | n | L1 / Y1 / R1 R2 R3 R4 / R5 R6 R7 R8 / R9 R10 R11 R12 | | | | X1 | X2 | X3 | X4 | X5 | X6 |
|---|---|---|---|---|---|---|---|---|---|---|---|---|---|
| 166 | Ir | 3 | 0 | K''' | | | | H | H | H | H | H | H |
| | | | | F | F | F | F | | | | | | |
| | | | | F | F | F | F | | | | | | |
| | | | | — | — | — | — | | | | | | |
| 167 | Ir | 3 | 0 | L''' | | | | H | H | H | OCH3 | H | H |
| | | | | F | F | F | F | | | | | | |
| | | | | F | F | F | F | | | | | | |
| | | | | — | — | — | — | | | | | | |
| 168 | Ir | 3 | 0 | M''' | | | | H | H | H | H | H | H |
| | | | | F | F | F | F | | | | | | |
| | | | | F | F | F | F | | | | | | |
| | | | | — | — | — | — | | | | | | |
| 169 | Ir | 3 | 0 | N''' | | | | H | H | H | N(Ph)2 | H | H |
| | | | | F | F | F | F | | | | | | |
| | | | | F | F | F | F | | | | | | |
| | | | | — | — | — | — | | | | | | |
| 170 | Ir | 3 | 0 | O''' | | | | H | H | H | H | H | H |
| | | | | F | F | F | F | | | | | | |
| | | | | F | F | F | F | | | | | | |
| | | | | — | — | — | — | | | | | | |
| 171 | Ir | 3 | 0 | P''' | | | | H | H | H | H | H | H |
| | | | | F | F | F | F | | | | | | |
| | | | | F | F | F | F | | | | | | |
| | | | | — | — | — | — | | | | | | |
| 172 | Ir | 3 | 0 | Q''' | | | | H | H | H | H | H | H |
| | | | | F | F | F | F | | | | | | |
| | | | | F | F | F | F | | | | | | |
| | | | | — | — | — | — | | | | | | |
| 173 | Ir | 3 | 0 | R''' | | | | H | H | H | N(CH3)2 | H | H |
| | | | | F | F | F | F | | | | | | |
| | | | | F | F | F | F | | | | | | |
| | | | | — | — | — | — | | | | | | |
| 174 | Ir | 3 | 0 | S''' | | | | H | H | H | H | H | H |
| | | | | F | F | F | F | | | | | | |
| | | | | F | F | F | F | | | | | | |
| | | | | — | — | — | — | | | | | | |
| 175 | Ir | 3 | 0 | T''' | | | | H | H | H | H | H | H |
| | | | | F | F | F | F | | | | | | |
| | | | | F | F | F | F | | | | | | |
| | | | | — | — | — | — | | | | | | |

TABLE 12-continued

| No | M | m | n | Y1 (R1 R2 R3 R4 / R5 R6 R7 R8 / R9 R10 R11 R12) | X1 | X2 | X3 | X4 | X5 | X6 |
|---|---|---|---|---|---|---|---|---|---|---|
| 176 | Pt | 2 | 0 | U''' ; F F F F / F F F F / — — — — | H | H | H | OC2H5 | H | H |
| 177 | Ir | 3 | 0 | V''' ; F F F F / F F F F / — — — — | H | H | H | H | H | H |
| 178 | Ir | 3 | 0 | W''' ; F F F F / F F F F / — — — — | H | H | H | H | H | H |
| 179 | Ir | 3 | 0 | X''' ; F F F F / F F F F / — — — — | H | H | H | OCH3 | H | H |
| 180 | Ir | 3 | 0 | Y''' ; F F F F / F F F F / — — — — | H | H | H | H | H | H |

TABLE 13

| No | M | m | n | Y1 (R1 R2 R3 R4 / R5 R6 R7 R8 / R9 R10 R11 R12) | X1 | X2 | X3 | X4 | X5 | X6 |
|---|---|---|---|---|---|---|---|---|---|---|
| 181 | Ir | 3 | 0 | Z''' ; F F F F / F F F F / — — — — | H | H | H | H | H | H |
| 182 | Ir | 3 | 0 | A'''' ; F F F F / F F F F / — — — — | H | H | H | N(CH3)2 | H | H |
| 183 | Ir | 3 | 0 | B'''' ; F F F F / F F F F / — — — — | H | H | H | OCH3 | H | H |
| 184 | Ir | 3 | 0 | C'''' ; F F F F / F F F F / — — — — | H | H | H | H | H | H |
| 185 | Rh | 3 | 0 | D'''' ; F F F F / F F F F / — — — — | H | H | H | H | H | H |

TABLE 14

| No | M | m | n | Y1 (R1 R2 R3 R4 / R5 R6 R7 R8 / R9 R10 R11 R12) | X1 | X2 | X3 | X4 | X5 | X6 | A1 (R1' R2' R3' R4') | B1 (R5' R6' R7' R8') |
|---|---|---|---|---|---|---|---|---|---|---|---|---|
| 186 | Ir | 2 | 1 | A; R9=F R10=F R11=F R12=F | H | H | H | H | H | H | Ph1; F H F H | Pi; H OCH3 H H |
| 187 | Ir | 2 | 1 | A; R9=F R10=F R11=F R12=F | H | H | H | OCH3 | H | H | Ph1; H CF3 F H | Pr; H OCH3 H — |
| 188 | Ir | 2 | 1 | B; R9=H R10=H R11=F R12=H / H F — — | F | H | H | C2H5 | H | H | Ph1; H CF3 F CF3 | Pi; H H H H |
| 189 | Ir | 2 | 1 | B; R9=F R10=F R11=F R12=F / F F — — | H | H | H | N(CH3)2 | H | H | Tn1; CF3 H — — | Pi; H OCH3 H H |
| 190 | Ir | 1 | 2 | B; R9=F R10=F R11=F R12=F / F F — — | H | H | H | H | H | H | Ph1; F H F H | Pi; H N(CH3)2 H H |
| 191 | Ir | 2 | 1 | C; R9=H R10=F R11=H R12=F | CF3 | H | H | H | H | H | Ph1; H CF3 CF3 H | Pi; H H H H |
| 192 | Ir | 2 | 1 | C; R9=F R10=F R11=F R12=F | H | H | H | H | H | H | Ph1; H CF3 F H | Py1; H H H — |
| 193 | Ir | 2 | 1 | D; R9=F R10=F R11=F R12=F | H | H | H | N(C2H5)2 | H | H | Ph1; F H F H | Pi; H OCH3 H H |
| 194 | Ir | 2 | 1 | E; R9=H R10=F R11=H R12=F | H | H | H | N(CH3)Ph | H | H | Ph1; H CF3 F H | Pi; H N(CH3)2 H H |
| 195 | Ir | 2 | 1 | E; R9=F R10=F R11=F R12=F | H | H | H | OC3H7 | H | H | Ph1; H CF3 F CF3 | Pr; H CH3 H — |
| 196 | Ir | 2 | 1 | F; R9=F R10=F R11=— R12=— | H | H | H | H | H | H | Tn2; F H — — | Pi; H H H H |
| 197 | Ir | 2 | 1 | G; R9=F R10=F R11=F R12=F | H | H | F | H | H | H | Np1; H C2F5 — — | Pi; H C2H5 H H |
| 198 | Ir | 2 | 1 | H; R9=F R10=F R11=F R12=F | H | H | H | OCH3 | H | H | Ph1; H CF3 F H | Py2; CH3 H H — |

TABLE 14-continued

| | | | | L1 | | | | | | | | | | | | L1' | | | | | | | |
| | | | | Y1 | | | | | | | | | | | | | | | | | | | |
| | | | | R1 R2 R3 R4 | | | | | | | | | | | | | | | A1 | | | B1 | |
| | | | | R5 R6 R7 R8 | | | | | | | | | | | | | | | | | | | |
| No | M | m | n | R9 R10 R11 R12 | X1 | X2 | X3 | X4 | X5 | X6 | R1' | R2' | R3' | R4' | R5' | R6' | R7' | R8' |
|---|---|---|---|---|---|---|---|---|---|---|---|---|---|---|---|---|---|---|
| 199 | Ir | 2 | 1 | I | H | OCF3 | H | H | H | H | Ph1 | | | | Pi | | | |
| | | | | F H H H | | | | | | | F | H | F | H | H | OCH3 | H | H |
| | | | | H H H H | | | | | | | | | | | | | | |
| 200 | Ir | 2 | 1 | I | H | CF3 | H | H | H | H | Ph1 | | | | Pi | | | |
| | | | | F H H H | | | | | | | H | CF3 | CF3 | H | H | H | H | H |
| | | | | F H H H | | | | | | | | | | | | | | |

TABLE 15

| | | | | L1 | | | | | | |
| | | | | Y1 | | | | | | |
| | | | | R1 R2 R3 R4 | | | | | | |
| | | | | R5 R6 R7 R8 | | | | | | |
| No | M | m | n | R9 R10 R11 R12 | X1 | X2 | X3 | X4 | X5 | X6 |
|---|---|---|---|---|---|---|---|---|---|---|
| 201 | Ir | 2 | 1 | I | H | H | H | H | H | H |
| | | | | F H H F | | | | | | |
| | | | | F H H F | | | | | | |
| 202 | Ir | 2 | 1 | I | H | H | H | N(CH3)2 | H | H |
| | | | | F H H F | | | | | | |
| | | | | F H H F | | | | | | |
| 203 | Ir | 2 | 1 | I | H | H | H | H | N(Ph)2 | H |
| | | | | F H H F | | | | | | |
| | | | | F H H F | | | | | | |
| 204 | Ir | 2 | 1 | I | H | H | H | N(CH3)Ph | H | H |
| | | | | F H H F | | | | | | |
| | | | | F H H F | | | | | | |
| 205 | Ir | 2 | 1 | I | CH3 | H | H | CH3 | H | H |
| | | | | F H H F | | | | | | |
| | | | | F H H F | | | | | | |
| 206 | Ir | 2 | 1 | I | H | H | H | H | H | CH3 |
| | | | | F H H F | | | | | | |
| | | | | F H H F | | | | | | |
| 207 | Ir | 2 | 1 | I | H | H | H | OC2H5 | H | H |
| | | | | F H H F | | | | | | |
| | | | | F H H F | | | | | | |
| 208 | Ir | 2 | 1 | I | H | H | H | H | N(C3H7)2 | H |
| | | | | F H H F | | | | | | |
| | | | | F H H F | | | | | | |
| 209 | Ir | 2 | 1 | J | H | H | H | H | OCH3 | H |
| | | | | H H F H | | | | | | |
| | | | | H F — — | | | | | | |

TABLE 15-continued

| No | | | | | | | | | | |
|---|---|---|---|---|---|---|---|---|---|---|
| 210 | Ir | 1 | 2 | J | H | H | H | H | H | H |
| | | | | F F — | F F — | F — — | F — — | | | |
| 211 | Ir | 2 | 1 | K | H | H | H | OC5H11 | H | H |
| | | | | F H — | H H — | H — — | F — — | | | |
| 212 | Ir | 2 | 1 | K | H | H | H | N(C3H7)2 | H | H |
| | | | | F H — | H F — | F — — | F — — | | | |
| 213 | Ir | 2 | 1 | L | H | H | H | N(N2p)Ph | H | H |
| | | | | F F — | F F — | F — — | F — — | | | |
| 214 | Ir | 2 | 1 | M | H | H | H | OCH3 | H | H |
| | | | | H H — | H F — | F — — | H — — | | | |
| 215 | Ir | 2 | 1 | N | H | H | H | H | H | H |
| | | | | H H — | H F — | F — — | H — — | | | |

| | L1' | | | | | | | |
|---|---|---|---|---|---|---|---|---|
| | A1 | | | | B1 | | | |
| No | R1' | R2' | R3' | R4' | R5' | R6' | R7' | R8' |
| 201 | Np2 | | | | Pi | | | |
| 202 | CF3 | CF3 Ph1 | — | — | H | N(CH3)2 Pi | H | H |
| 203 | H | CF3 Ph1 | F | H | H | CH3 Pi | H | H |
| 204 | H | OCF3 Ph1 | F | H | H | OCH3 Pr | H | H |
| 205 | F | H Ph1 | F | H | H | N(CH3)2 Pi | H | — |
| 206 | H | CF3 Ph1 | F | CF3 | H | H Pi | N(Ph)2 | H |
| 207 | H | CF3 Ph1 | F | H | H | H Py1 | H | H |
| 208 | H | CF3 Np2 | CF3 | H | H | C5H11 Pi | H | — |
| 209 | OCF3 | OCF3 Ph1 | — | — | H | N(CH3)2 Pi | H | H |
| 210 | F | H Ph1 | F | H | H | OCH3 Pi | H | H |
| 211 | H | OCF3 Np1 | F | H | H | H Pr | H | H |
| 212 | CH3 | CF3 Ph1 | — | — | H | H Pr | H | — |
| 213 | H | CF3 Ph1 | F | H | H | H Pi | H | — |
| | H | CF3 | F | CF3 | H | CH3 | H | H |

TABLE 15-continued

| No | Ph1 | | | | Py2 | | | |
|---|---|---|---|---|---|---|---|---|
| 214 | F | H | F | H | H | H | H | — |
| No | Ph1 | | | | Pi | | | |
| 215 | H | CF3 | F | H | H | OCH3 | H | H |

TABLE 16

| No | M | m | n | L1 Y1 R1/R5/R9 | R2/R6/R10 | R3/R7/R11 | R4/R8/R12 | X1 | X2 | X3 | X4 | X5 | X6 |
|---|---|---|---|---|---|---|---|---|---|---|---|---|---|
| 216 | Ir | 2 | 1 | O | | | | H | H | H | OCH3 | H | H |
| | | | | F / F / — | F / F / — | F / — / — | F / — / — | | | | | | |
| 217 | Ir | 1 | 2 | P | | | | H | H | H | H | H | H |
| | | | | F / F / — | F / F / — | F / — / — | F / — / — | | | | | | |
| 218 | Ir | 2 | 1 | R | | | | H | H | H | OCH3 | H | H |
| | | | | H / — / — | F / — / — | H / — / — | F / — / — | | | | | | |
| 219 | Ir | 2 | 1 | R | | | | H | H | H | H | H | H |
| | | | | F / — / — | F / — / — | F / — / — | F / — / — | | | | | | |
| 220 | Ir | 2 | 1 | R | | | | H | H | H | OC6H13 | H | H |
| | | | | F / — / — | F / — / — | F / — / — | F / — / — | | | | | | |
| 221 | Ir | 2 | 1 | R | | | | H | H | H | N(CH3)Ph | H | H |
| | | | | F / — / — | F / — / — | F / — / — | F / — / — | | | | | | |
| 222 | Ir | 2 | 1 | R | | | | H | H | H | CH3 | H | H |
| | | | | F / — / — | F / — / — | F / — / — | F / — / — | | | | | | |
| 223 | Ir | 2 | 1 | S | | | | H | H | H | H | H | H |
| | | | | F / — / — | F / — / — | F / — / — | F / — / — | | | | | | |
| 224 | Ir | 2 | 1 | S | | | | H | H | H | OCH3 | H | H |
| | | | | F / — / — | F / — / — | F / — / — | F / — / — | | | | | | |
| 225 | Ir | 2 | 1 | S | | | | H | H | H | N(Ph)2 | H | H |
| | | | | F / — / — | F / — / — | F / — / — | F / — / — | | | | | | |
| 226 | Ir | 2 | 1 | T | | | | H | F | H | H | H | H |
| | | | | F / — / — | H / — / — | F / — / — | H / — / — | | | | | | |
| 227 | Ir | 2 | 1 | U | | | | H | H | H | H | H | H |
| | | | | F / F / F | F / F / F | F / F / — | F / F / — | | | | | | |

TABLE 16-continued

| No | | | | | | | | | | | | |
|----|----|----|----|----|----|----|----|----|----|----|----|----|
| 228 | Ir | 2 | 1 | X | | | | H | H | H | H | H | OCH3 |
| | | | | F F — — | F F — — | F F — — | F F — — | | | | | | |
| 229 | Ir | 1 | 2 | C' | | | | H | H | H | H | H | H |
| | | | | F F — — | F F — — | F — — — | F — — — | | | | | | |
| 230 | Ir | 2 | 1 | G' | | | | H | H | H | H | H | H |
| | | | | F — — | F — — | F — — | F — — | | | | | | |

| | L1' | | | | | | | |
|----|----|----|----|----|----|----|----|----|
| | A1 | | | | B1 | | | |
| No | R1' | R2' | R3' | R4' | R5' | R6' | R7' | R8' |
| 216 | Cn1 | | | | Py1 | | | |
| 217 | CF3 Ph1 | — | — | — | H Pi | H | H | — |
| 218 | H Ph1 | CF3 | F | CF3 | H Pi | N(CH3)2 | H | H |
| 219 | H Cn2 | CF3 | F | H | H Pi | H | H | H |
| 220 | C3F7 Ph1 | — | — | — | H Py1 | OCH3 | H | H |
| 221 | F Ph1 | H | F | H | H Pi | N(Ph)2 | H | — |
| 222 | H Ph1 | OCF3 | F | H | H Pi | H | N(CH3)2 | H |
| 223 | H Ph1 | CF3 | CF3 | H | H Pr | CH3 | H | H |
| 224 | F Qn1 | CF3 | F | H | H Pi | H | H | — |
| 225 | Cl Ph1 | F | — | — | H Pi | H | H | H |
| 226 | F Ph1 | H | F | H | H Pi | N(CH3)2 | H | H |
| 227 | H Ph1 | CF3 | F | H | H Py2 | OCH3 | H | H |
| 228 | H Ph1 | CF3 | F | CF3 | H Pi | H | CH3 | — |
| 229 | F Ph1 | CF3 | F | H | H Py2 | H | H | H |
| 230 | H Ph1 | CF3 | F | H | H Pi | OC2H5 | H | — |
| | F | H | F | H | H | OCH3 | F | H |

TABLE 17

| No | M | m | n | Y1 R1/R5/R9 | Y1 R2/R6/R10 | Y1 R3/R7/R11 | Y1 R4/R8/R12 | X1 | X2 | X3 | X4 | X5 | X6 |
|---|---|---|---|---|---|---|---|---|---|---|---|---|---|
| 231 | Ir | 2 | 1 | _____ J' _____ | | | | H | H | H | N(C3H7)2 | H | H |
|  |  |  |  | F F — | F F — | F F — | F F — | | | | | | |
| 232 | Ir | 2 | 1 | _____ M' _____ | | | | H | H | H | H | H | H |
|  |  |  |  | F F — | F F — | F — — | F — — | | | | | | |
| 233 | Ir | 1 | 2 | _____ W' _____ | | | | H | H | H | N(Ph)2 | H | H |
|  |  |  |  | F — — | F — — | F — — | F — — | | | | | | |
| 234 | Ir | 2 | 1 | _____ E'' _____ | | | | H | H | H | H | H | H |
|  |  |  |  | F — — | F — — | F — — | F — — | | | | | | |
| 235 | Ir | 2 | 1 | _____ I'' _____ | | | | H | H | H | N(CH3)2 | H | H |
|  |  |  |  | F — — | F — — | F — — | F — — | | | | | | |
| 236 | Ir | 2 | 1 | _____ W'' _____ | | | | H | H | H | OCH3 | H | OCH3 |
|  |  |  |  | F F — | F F — | F — — | F — — | | | | | | |
| 237 | Pt | 1 | 1 | _____ X'' _____ | | | | H | CF3 | H | H | H | H |
|  |  |  |  | F F — | F F — | F — — | F — — | | | | | | |
| 238 | Ir | 2 | 1 | _____ Y'' _____ | | | | H | H | H | N(Ph)2 | H | H |
|  |  |  |  | F F — | F F — | F — — | F — — | | | | | | |
| 239 | Ir | 2 | 1 | _____ B''' _____ | | | | H | H | H | H | H | H |
|  |  |  |  | F F — | F F — | F — — | F — — | | | | | | |
| 240 | Pd | 1 | 1 | _____ D''' _____ | | | | H | H | H | H | N(CH3)2 | H |
|  |  |  |  | F F F | F F F | F F F | F F F | | | | | | |
| 241 | Ir | 2 | 1 | _____ F''' _____ | | | | H | H | H | OCH3 | H | H |
|  |  |  |  | F F F | F F F | F F — | F F — | | | | | | |
| 242 | Ir | 2 | 1 | _____ H''' _____ | | | | H | H | H | OC4H9 | H | H |
|  |  |  |  | F F F | F F F | F F — | F F — | | | | | | |
| 243 | Rh | 2 | 1 | _____ U''' _____ | | | | H | H | H | OC2H5 | H | H |
|  |  |  |  | F F — | F F — | F F — | F F — | | | | | | |
| 244 | Ir | 2 | 1 | _____ W''' _____ | | | | H | H | H | H | H | H |
|  |  |  |  | F F — | F F — | F — — | F — — | | | | | | |

TABLE 17-continued

| No | M | m | n | | | | | R9 | R10 | R11 | R12 | X5 | X6 |
|---|---|---|---|---|---|---|---|---|---|---|---|---|---|
| 245 | Ir | 2 | 1 | A"" | | | | H | H | H | N(CH3)2 | H | H |
| | | | | F | F | F | F | | | | | | |
| | | | | F | F | F | F | | | | | | |
| | | | | — | — | — | — | | | | | | |

| | | L1' | | | | | | | |
|---|---|---|---|---|---|---|---|---|---|
| | | A1 | | | | B1 | | | |
| No | R1' | R2' | R3' | R4' | R5' | R6' | R7' | R8' | |
| 231 | | Ph1 | | | | Pr | | | |
| 232 | H | OCF3 | F | H | H | C3H7 | H | — | |
| | | Qn2 | | | | Pi | | | |
| 233 | H | H | — | — | H | OCH3 | H | H | |
| | | Ph1 | | | | Pi | | | |
| 234 | H | CF3 | F | H | H | CH3 | H | H | |
| | | Ph1 | | | | Pi | | | |
| 235 | H | CF3 | CF3 | H | H | H | H | H | |
| | | Ph1 | | | | Pi | | | |
| 236 | F | H | F | H | H | N(CH3)2 | H | H | |
| | | Ph1 | | | | Py1 | | | |
| 237 | H | CF3 | F | CF3 | H | H | H | — | |
| | | Np2 | | | | Pi | | | |
| 238 | OCF3 | OCF3 | — | — | H | OCH3 | H | H | |
| | | Ph1 | | | | Pi | | | |
| 239 | H | CF3 | F | H | H | OC4H9 | H | H | |
| | | Ph1 | | | | Py2 | | | |
| 240 | F | CF3 | F | H | H | H | H | — | |
| | | Ph1 | | | | Pi | | | |
| 241 | F | H | F | H | H | CH3 | H | H | |
| | | Ph1 | | | | Py2 | | | |
| 242 | H | OCF3 | F | H | H | OCH3 | H | — | |
| | | Ph1 | | | | Pr | | | |
| 243 | H | CF3 | F | H | H | H | H | — | |
| | | Ph1 | | | | Pi | | | |
| 244 | H | CF3 | F | CF3 | H | H | H | H | |
| | | Ph1 | | | | Pi | | | |
| 245 | F | H | F | H | H | N(CH3)2 | H | H | |
| | | Ph1 | | | | Pi | | | |
| | H | CF3 | F | H | H | OCH3 | H | H | |

TABLE 18

| | | | | L1 | | | | | | | | | | | | | | | |
|---|---|---|---|---|---|---|---|---|---|---|---|---|---|---|---|---|---|---|---|
| | | | | Y1 | | | | | | | | | | | | | L1' | | |
| | | | | R1 | R2 | R3 | R4 | | | | | | | | | | B2 | | |
| | | | | R5 | R6 | R7 | R8 | | | | | | | | | | | | |
| No | M | m | n | R9 | R10 | R11 | R12 | X1 | X2 | X3 | X4 | X5 | X6 | R5' | R6' | R7' | R8' | | |
| 246 | Ir | 2 | 1 | A | | | | H | H | H | H | H | H | | Pi | | | | |
| | | | | F | F | F | F | | | | | | | H | H | H | H | | |
| | | | | — | — | — | — | | | | | | | | | | | | |

TABLE 18-continued

| | | | | | | | | | | | | | | | | |
|---|---|---|---|---|---|---|---|---|---|---|---|---|---|---|---|---|
| | | | | L1 | | | | | | | | | | L1' | | |
| | | | | Y1 | | | | | | | | | | B2 | | |
| | | | | R1 R2 R3 R4 | | | | | | | | | | | | |
| | | | | R5 R6 R7 R8 | | | | | | | | | | | | |
| No | M | m | n | R9 R10 R11 R12 | | | | X1 | X2 | X3 | X4 | X5 | X6 | R5' R6' R7' R8' | | |
| 247 | Ir | 2 | 1 | A | | | | H | H | H | OCH3 | H | H | Pi | | |
| | | | | F | F | F | F | | | | | | | H | H | H | H |
| 248 | Ir | 2 | 1 | B | | | | F | H | H | C2H5 | H | H | Pr | | |
| | | | | H | H | F | H | | | | | | | H | H | H | — |
| | | | | H | F | — | — | | | | | | | | | | |
| 249 | Ir | 2 | 1 | B | | | | H | H | H | N(CH3)2 | H | H | Pi | | |
| | | | | F | F | F | F | | | | | | | H | H | H | H |
| | | | | F | F | — | — | | | | | | | | | | |
| 250 | Ir | 2 | 1 | B | | | | H | H | H | H | H | H | Pi | | |
| | | | | F | F | F | F | | | | | | | H | H | H | CH3 |
| | | | | F | F | — | — | | | | | | | | | | |
| 251 | Ir | 2 | 1 | C | | | | CF3 | H | H | H | H | H | Py1 | | |
| | | | | H | F | H | F | | | | | | | H | H | H | — |
| 252 | Ir | 2 | 1 | C | | | | H | H | H | H | H | H | Pi | | |
| | | | | F | F | F | F | | | | | | | H | H | H | H |
| 253 | Ir | 2 | 1 | D | | | | H | H | H | N(C2H5)2 | H | H | Pi | | |
| | | | | F | F | F | F | | | | | | | H | H | H | H |
| 254 | Ir | 2 | 1 | E | | | | H | H | H | N(CH3)Ph | H | H | Py2 | | |
| | | | | H | F | H | F | | | | | | | H | H | H | — |
| 255 | Ir | 2 | 1 | E | | | | H | H | H | OC3H7 | H | H | Pi | | |
| | | | | F | F | F | F | | | | | | | H | H | H | CH3 |
| 256 | Ir | 2 | 1 | F | | | | H | H | H | H | H | H | Pi | | |
| | | | | F | F | — | — | | | | | | | H | H | H | H |
| 257 | Ir | 2 | 1 | G | | | | H | H | F | H | H | H | Pr | | |
| | | | | F | F | F | F | | | | | | | H | H | H | — |
| 258 | Ir | 2 | 1 | H | | | | H | H | H | OCH3 | H | H | Pi | | |
| | | | | F | F | F | F | | | | | | | H | H | H | H |
| 259 | Ir | 2 | 1 | I | | | | H | OCF3 | H | H | H | H | Pi | | |
| | | | | F | H | H | H | | | | | | | H | H | H | CH3 |
| | | | | H | H | H | H | | | | | | | | | | |
| 260 | Ir | 2 | 1 | I | | | | H | CF3 | H | H | H | H | Py1 | | |
| | | | | F | H | H | H | | | | | | | H | H | H | — |
| | | | | F | H | H | H | | | | | | | | | | |

TABLE 19

| | | | | L1 | | | | | | | | | | | L1' B2 | | | |
|---|---|---|---|---|---|---|---|---|---|---|---|---|---|---|---|---|---|---|
| | | | | Y1 | | | | | | | | | | | | | | |
| | | | | R1 R5 | R2 R6 | R3 R7 | R4 R8 | | | | | | | | | | | |
| No | M | m | n | R9 | R10 | R11 | R12 | X1 | X2 | X3 | X4 | X5 | X6 | | R5' | R6' | R7' | R8' |
| 261 | Ir | 2 | 1 | | I | | | H | H | H | H | H | H | | Pi | | | |
| | | | | F F | H H | H H | F F | | | | | | | | H | H | H | H |
| 262 | Ir | 2 | 1 | | I | | | H | H | H | N(CH3)2 | H | H | | Pi | | | |
| | | | | F F | H H | H H | F F | | | | | | | | H | H | H | H |
| 263 | Ir | 2 | 1 | | I | | | H | H | H | H | N(Ph)2 | H | | Py2 | | | |
| | | | | F F | H H | H H | F F | | | | | | | | H | H | H | — |
| 264 | Ir | 2 | 1 | | I | | | H | H | H | N(CH3)Ph | H | H | | Pi | | | |
| | | | | F F | H H | H H | F F | | | | | | | | H | H | CH3 | H |
| 265 | Ir | 2 | 1 | | I | | | CH3 | H | H | CH3 | H | H | | Pi | | | |
| | | | | F F | H H | H H | F F | | | | | | | | H | H | H | H |
| 266 | Ir | 2 | 1 | | I | | | H | H | H | H | H | CH3 | | Pi | | | |
| | | | | F F | H H | H H | F F | | | | | | | | H | H | H | CF3 |
| 267 | Ir | 2 | 1 | | I | | | H | H | H | OC2H5 | H | H | | Pi | | | |
| | | | | F F | H H | H H | F F | | | | | | | | H | F | H | H |
| 268 | Ir | 2 | 1 | | I | | | H | H | H | H | N(C3H7)2 | H | | Pi | | | |
| | | | | F F | H H | H H | F F | | | | | | | | H | H | H | CH3 |
| 269 | Ir | 2 | 1 | | J | | | H | H | H | H | OCH3 | H | | Py1 | | | |
| | | | | H H | H F | F — | H — | | | | | | | | H | H | H | — |
| 270 | Ir | 2 | 1 | | J | | | H | H | H | H | H | H | | Pi | | | |
| | | | | F F | F F | F — | F — | | | | | | | | H | H | H | H |
| 271 | Ir | 2 | 1 | | K | | | H | H | H | OC5H11 | H | H | | Pi | | | |
| | | | | F H | H H | H — | F — | | | | | | | | H | H | H | H |
| 272 | Ir | 2 | 1 | | K | | | H | H | H | N(C3H7)2 | H | H | | Pi | | | |
| | | | | F H | H F | F — | F — | | | | | | | | H | H | H | F |
| 273 | Ir | 2 | 1 | | L | | | H | H | H | N(N2p)Ph | H | H | | Pi | | | |
| | | | | F F | F F | F — | F — | | | | | | | | H | H | CH3 | H |
| 274 | Ir | 2 | 1 | | M | | | H | H | H | OCH3 | H | H | | Pi | | | |
| | | | | H H | H F | F — | H — | | | | | | | | H | H | H | H |

TABLE 19-continued

| No | M | m | n | R1/R5/R9 | R2/R6/R10 | R3/R7/R11 | R4/R8/R12 | Y1 | X1 | X2 | X3 | X4 | X5 | X6 | B2 | R5' | R6' | R7' | R8' |
|---|---|---|---|---|---|---|---|---|---|---|---|---|---|---|---|---|---|---|---|
| 275 | Ir | 2 | 1 | H / H / — | H / F / — | F / — / — | H / — / — | N | H | H | H | H | H | H | Pr | H | H | H | — |

TABLE 20

| No | M | m | n | R1/R5/R9 | R2/R6/R10 | R3/R7/R11 | R4/R8/R12 | Y1 | X1 | X2 | X3 | X4 | X5 | X6 | B2 | R5' | R6' | R7' | R8' |
|---|---|---|---|---|---|---|---|---|---|---|---|---|---|---|---|---|---|---|---|
| 276 | Ir | 2 | 1 | F / F / — | F / F / — | F / — / — | F / — / — | O | H | H | H | OCH3 | H | H | Pi | H | H | H | H |
| 277 | Ir | 2 | 1 | F / F / — | F / F / — | F / — / — | F / — / — | P | H | H | H | H | H | H | Pi | H | H | H | H |
| 278 | Ir | 2 | 1 | H / — / — | F / — / — | H / — / — | F / — / — | R | H | H | H | OCH3 | H | H | Py1 | H | H | H | — |
| 279 | Ir | 2 | 1 | F / — / — | F / — / — | F / — / — | F / — / — | R | H | H | H | H | H | H | Pi | H | H | H | CH3 |
| 280 | Ir | 2 | 1 | F / — / — | F / — / — | F / — / — | F / — / — | R | H | H | H | OC6H13 | H | H | Pi | H | H | H | H |
| 281 | Ir | 2 | 1 | F / — / — | F / — / — | F / — / — | F / — / — | R | H | H | H | N(CH3)Ph | H | H | Py2 | H | H | H | — |
| 282 | Ir | 2 | 1 | F / — / — | F / — / — | F / — / — | F / — / — | R | H | H | H | CH3 | H | H | Pi | H | H | CH3 | H |
| 283 | Ir | 2 | 1 | F / — / — | F / — / — | F / — / — | F / — / — | S | H | H | H | H | H | H | Pi | H | H | H | H |
| 284 | Ir | 2 | 1 | F / — / — | F / — / — | F / — / — | F / — / — | S | H | H | H | OCH3 | H | H | Pi | H | H | CF3 | H |
| 285 | Ir | 2 | 1 | F / — / — | F / — / — | F / — / — | F / — / — | S | H | H | H | N(Ph)2 | H | H | Pi | H | H | H | H |

TABLE 20-continued

| No | M | m | n | R1/R5/R9 | R2/R6/R10 | R3/R7/R11 | R4/R8/R12 | X1 | X2 | X3 | X4 | X5 | X6 | R5' | R6' | R7' | R8' |
|---|---|---|---|---|---|---|---|---|---|---|---|---|---|---|---|---|---|
| 286 | Ir | 2 | 1 | | T | | | H | F | H | H | H | H | | Pi | | |
| | | | | F | H | F | H | | | | | | | H | H | H | H |
| | | | | — | — | — | — | | | | | | | | | | |
| 287 | Ir | 2 | 1 | | U | | | H | H | H | H | H | H | | Py1 | | |
| | | | | F | F | F | F | | | | | | | H | H | H | — |
| | | | | F | F | F | F | | | | | | | | | | |
| | | | | F | F | — | — | | | | | | | | | | |
| 288 | Ir | 2 | 1 | | X | | | H | H | H | H | H | OCH3 | | Pi | | |
| | | | | F | F | F | F | | | | | | | H | H | H | CH3 |
| | | | | F | F | F | F | | | | | | | | | | |
| 289 | Ir | 2 | 1 | | C' | | | H | H | H | H | H | H | | Pi | | |
| | | | | F | F | F | F | | | | | | | H | H | H | H |
| | | | | F | F | — | — | | | | | | | | | | |
| | | | | — | — | | | | | | | | | | | | |
| 290 | Ir | 2 | 1 | | G' | | | H | H | H | H | H | H | | Pr | | |
| | | | | F | F | F | F | | | | | | | H | H | H | — |
| | | | | — | — | — | — | | | | | | | | | | |

TABLE 21

| No | M | m | n | R1/R5/R9 | R2/R6/R10 | R3/R7/R11 | R4/R8/R12 | X1 | X2 | X3 | X4 | X5 | X6 | R5' | R6' | R7' | R8' |
|---|---|---|---|---|---|---|---|---|---|---|---|---|---|---|---|---|---|
| 291 | Ir | 2 | 1 | | J' | | | H | H | H | N(C3H7)2 | H | H | | Pi | | |
| | | | | F | F | F | F | | | | | | | H | H | H | H |
| | | | | F | F | F | F | | | | | | | | | | |
| | | | | — | | | | | | | | | | | | | |
| 292 | Ir | 2 | 1 | | M' | | | H | H | H | H | H | H | | Pi | | |
| | | | | F | F | F | F | | | | | | | H | H | H | H |
| | | | | F | F | — | — | | | | | | | | | | |
| 293 | Ir | 2 | 1 | | W' | | | H | H | H | N(Ph)2 | H | H | | Py2 | | |
| | | | | F | F | F | F | | | | | | | H | H | H | — |
| | | | | — | — | | | | | | | | | | | | |
| 294 | Ir | 2 | 1 | | E" | | | H | H | H | H | H | H | | Pi | | |
| | | | | F | F | F | F | | | | | | | H | H | H | H |
| | | | | — | — | | | | | | | | | | | | |
| 295 | Ir | 2 | 1 | | I" | | | H | H | H | N(CH3)2 | H | H | | Pi | | |
| | | | | F | F | F | F | | | | | | | H | H | H | CH3 |
| | | | | — | — | | | | | | | | | | | | |
| 296 | Ir | 2 | 1 | | W" | | | H | H | H | OCH3 | H | OCH3 | | Py1 | | |
| | | | | F | F | F | F | | | | | | | H | H | H | — |
| | | | | F | F | — | — | | | | | | | | | | |

TABLE 21-continued

| | | | | L1 | | | | | | | | | | | L1' | | | |
| | | | | Y1 | | | | | | | | | | | B2 | | | |
| | | | | R1 R2 R3 R4 | | | | | | | | | | | | | | |
| | | | | R5 R6 R7 R8 | | | | | | | | | | | | | | |
| No | M | m | n | R9 | R10 | R11 | R12 | X1 | X2 | X3 | X4 | X5 | X6 | R5' | R6' | R7' | R8' |
|---|---|---|---|---|---|---|---|---|---|---|---|---|---|---|---|---|---|
| 297 | Ir | 2 | 1 | | X'' | | | H | CF3 | H | H | H | H | | Pi | | |
| | | | | F | F | F | F | | | | | | | H | H | H | H |
| | | | | F | F | — | — | | | | | | | | | | |
| 298 | Ir | 2 | 1 | | Y'' | | | H | H | H | N(Ph)2 | H | H | | Pi | | |
| | | | | F | F | F | F | | | | | | | H | H | H | H |
| | | | | F | F | — | — | | | | | | | | | | |
| 299 | Ir | 2 | 1 | | B''' | | | H | H | H | H | H | H | | Pi | | |
| | | | | F | F | F | F | | | | | | | H | H | OCH3 | H |
| | | | | F | F | — | — | | | | | | | | | | |
| 300 | Ir | 2 | 1 | | D''' | | | H | H | H | H | N(CH3)2 | H | | Pi | | |
| | | | | F | F | F | F | | | | | | | H | H | H | CH3 |
| | | | | F | F | F | F | | | | | | | | | | |
| 301 | Ir | 2 | 1 | | F''' | | | H | H | H | OCH3 | H | H | | Pi | | |
| | | | | F | F | F | F | | | | | | | H | H | H | H |
| | | | | F | F | — | — | | | | | | | | | | |
| 302 | Ir | 2 | 1 | | H''' | | | H | H | H | OC4H9 | H | H | | Pr | | |
| | | | | F | F | F | F | | | | | | | H | H | H | — |
| | | | | F | F | — | — | | | | | | | | | | |
| 303 | Ir | 2 | 1 | | U''' | | | H | H | H | OC2H5 | H | H | | Pi | | |
| | | | | F | F | F | F | | | | | | | H | H | H | H |
| | | | | F | F | F | F | | | | | | | | | | |
| 304 | Ir | 2 | 1 | | W''' | | | H | H | H | H | H | H | | Pi | | |
| | | | | F | F | F | F | | | | | | | H | H | H | H |
| | | | | F | F | F | F | | | | | | | | | | |
| 305 | Ir | 2 | 1 | | A'''' | | | H | H | H | N(CH3)2 | H | H | | Py1 | | |
| | | | | F | F | F | F | | | | | | | H | H | H | — |
| | | | | F | F | F | F | | | | | | | | | | |

TABLE 22

| | | | | L1 | | | | | | | | | | | | |
| | | | | Y1 | | | | | | | | | L1' | | | |
| | | | | R1 R2 R3 R4 | | | | | | | | | | | | |
| | | | | R5 R6 R7 R8 | | | | | | | | | | | | |
| No | M | m | n | R9 | R10 | R11 | R12 | X1 | X2 | X3 | X4 | X5 | X6 | E1 | J1 | G1 |
|---|---|---|---|---|---|---|---|---|---|---|---|---|---|---|---|---|
| 306 | Ir | 2 | 1 | | A | | | H | H | H | H | H | H | CH3 | H | CH3 |
| | | | | F | F | F | F | | | | | | | | | |
| | | | | — | — | — | — | | | | | | | | | |
| 307 | Ir | 2 | 1 | | A | | | H | H | H | OCH3 | H | H | C(CH3)3 | H | C(CH3)3 |
| | | | | F | F | F | F | | | | | | | | | |
| | | | | — | — | — | — | | | | | | | | | |

TABLE 22-continued

| | | | | L1 | | | | | | | | | | | L1' | | |
| | | | | Y1 | | | | | | | | | | | | | |
| | | | | R1 R5 | R2 R6 | R3 R7 | R4 R8 | | | | | | | | | | |
| No | M | m | n | R9 | R10 | R11 | R12 | X1 | X2 | X3 | X4 | X5 | X6 | E1 | J1 | G1 |
|---|---|---|---|---|---|---|---|---|---|---|---|---|---|---|---|---|
| 308 | Ir | 2 | 1 | | | B | | F | H | H | C2H5 | H | H | CH3 | H | CH3 |
| | | | | H H — | H F — | F — — | H — — | | | | | | | | | |
| 309 | Ir | 2 | 1 | | | B | | H | H | H | N(CH3)2 | H | H | OCH3 | H | OCH3 |
| | | | | F F — | F F — | F — — | F — — | | | | | | | | | |
| 310 | Ir | 2 | 1 | | | B | | H | H | H | H | H | H | CH3 | H | CH3 |
| | | | | F F — | F F — | F — — | F — — | | | | | | | | | |
| 311 | Ir | 2 | 1 | | | C | | CF3 | H | H | H | H | H | C(CH3)3 | H | C(CH3)3 |
| | | | | H — — | F — — | H — — | F — — | | | | | | | | | |
| 312 | Ir | 2 | 1 | | | C | | H | H | H | H | H | H | CH3 | H | CH3 |
| | | | | F — — | F — — | F — — | F — — | | | | | | | | | |
| 313 | Ir | 2 | 1 | | | D | | H | H | H | N(C2H5)2 | H | H | Ph | H | Ph |
| | | | | F — — | F — — | F — — | F — — | | | | | | | | | |
| 314 | Ir | 2 | 1 | | | E | | H | H | H | N(CH3)Ph | H | H | CH3 | H | CH3 |
| | | | | H — — | F — — | H — — | F — — | | | | | | | | | |
| 315 | Ir | 2 | 1 | | | E | | H | H | H | OC3H7 | H | H | C(CH3)3 | H | C(CH3)3 |
| | | | | F — — | F — — | F — — | F — — | | | | | | | | | |
| 316 | Ir | 2 | 1 | | | F | | H | H | H | H | H | H | CH3 | H | CH3 |
| | | | | F — — | F — — | — — — | — — — | | | | | | | | | |
| 317 | Ir | 2 | 1 | | | G | | H | H | F | H | H | H | OCH3 | H | OCH3 |
| | | | | F — — | F — — | F — — | F — — | | | | | | | | | |
| 318 | Ir | 2 | 1 | | | H | | H | H | H | OCH3 | H | H | CH3 | H | CH3 |
| | | | | F — — | F — — | F — — | F — — | | | | | | | | | |
| 319 | Ir | 2 | 1 | | | I | | H | OCF3 | H | H | H | H | C(CH3)3 | H | C(CH3)3 |
| | | | | F H — | H H — | H H — | H H — | | | | | | | | | |
| 320 | Ir | 2 | 1 | | | I | | H | CF3 | H | H | H | H | CH3 | H | CH3 |
| | | | | F F — | H H — | H H — | H H — | | | | | | | | | |

TABLE 23

| | | | | L1 | | | | | | | | | | L1' | | |
|---|---|---|---|---|---|---|---|---|---|---|---|---|---|---|---|---|
| | | | | Y1 | | | | | | | | | | | | |
| | | | | R1 R5 | R2 R6 | R3 R7 | R4 R8 | | | | | | | | | |
| No | M | m | n | R9 | R10 | R11 | R12 | X1 | X2 | X3 | X4 | X5 | X6 | E1 | J1 | G1 |
| 321 | Ir | 2 | 1 | | | I | | H | H | H | H | H | H | CH3 | H | CH3 |
| | | | | F F — | H H — | H H — | F F — | | | | | | | | | |
| 322 | Ir | 2 | 1 | | | I | | H | H | H | N(CH3)2 | H | H | OC2H5 | H | OC2H5 |
| | | | | F F — | H H — | H H — | F F — | | | | | | | | | |
| 323 | Ir | 2 | 1 | | | I | | H | H | H | H | N(Ph)2 | | CH3 | H | CH3 |
| | | | | F F — | H H — | H H — | F F — | | | | | | | | | |
| 324 | Ir | 2 | 1 | | | I | | H | H | H | N(CH3)Ph | H | H | C(CH3)3 | H | C(CH3)3 |
| | | | | F F — | H H — | H H — | F F — | | | | | | | | | |
| 325 | Ir | 2 | 1 | | | I | | CH3 | H | H | CH3 | H | H | CH3 | H | CH3 |
| | | | | F F — | H H — | H H — | F F — | | | | | | | | | |
| 326 | Ir | 2 | 1 | | | I | | H | H | H | H | H | CH3 | Ph | H | Ph |
| | | | | F F — | H H — | H H — | F F — | | | | | | | | | |
| 327 | Ir | 2 | 1 | | | I | | H | H | H | OC2H5 | H | H | CH3 | H | CH3 |
| | | | | F F — | H H — | H H — | F F — | | | | | | | | | |
| 328 | Ir | 2 | 1 | | | I | | H | H | H | H | N(C3H7)2 | H | C(CH3)3 | H | C(CH3)3 |
| | | | | F F — | H H — | H H — | F F — | | | | | | | | | |
| 329 | Ir | 2 | 1 | | | J | | H | H | H | H | OCH3 | H | CH3 | H | CH3 |
| | | | | H H — | H F — | F — — | H — — | | | | | | | | | |
| 330 | Ir | 2 | 1 | | | J | | H | H | H | H | H | H | OCH3 | H | OCH3 |
| | | | | F F — | F F — | F — — | F — — | | | | | | | | | |
| 331 | Ir | 2 | 1 | | | K | | H | H | H | OC5H11 | H | H | C(CH3)3 | H | C(CH3)3 |
| | | | | F H — | H H — | H — — | F — — | | | | | | | | | |
| 332 | Ir | 2 | 1 | | | K | | H | H | H | N(C3H7)2 | H | H | CH3 | H | CH3 |
| | | | | F H — | H F — | F — — | F — — | | | | | | | | | |
| 333 | Ir | 2 | 1 | | | L | | H | H | H | N(N2p)Ph | H | H | CH3 | H | CH3 |
| | | | | F F — | F F — | F — — | F — — | | | | | | | | | |
| 334 | Ir | 2 | 1 | | | M | | H | H | H | OCH3 | H | H | C(CH3)3 | H | C(CH3)3 |
| | | | | H H — | H F — | F — — | H — — | | | | | | | | | |

TABLE 23-continued

| No | M | m | n | L1 / Y1 / R1 R2 R3 R4 / R5 R6 R7 R8 / R9 R10 R11 R12 | | | | X1 | X2 | X3 | X4 | X5 | X6 | L1' / E1 | J1 | G1 |
|---|---|---|---|---|---|---|---|---|---|---|---|---|---|---|---|---|
| 335 | Ir | 2 | 1 | N | | | | H | H | H | H | H | H | CH3 | H | CH3 |
|  |  |  |  | H | H | F | H |  |  |  |  |  |  |  |  |  |
|  |  |  |  | H | F | — | — |  |  |  |  |  |  |  |  |  |
|  |  |  |  | — | — | — | — |  |  |  |  |  |  |  |  |  |

TABLE 24

| No | M | m | n | L1 / Y1 / R1 R2 R3 R4 / R5 R6 R7 R8 / R9 R10 R11 R12 | | | | X1 | X2 | X3 | X4 | X5 | X6 | L1' / E1 | J1 | G1 |
|---|---|---|---|---|---|---|---|---|---|---|---|---|---|---|---|---|
| 336 | Ir | 2 | 1 | O | | | | H | H | H | OCH3 | H | H | CH3 | H | CH3 |
|  |  |  |  | F | F | F | F |  |  |  |  |  |  |  |  |  |
|  |  |  |  | F | F | — | — |  |  |  |  |  |  |  |  |  |
|  |  |  |  | — | — | — | — |  |  |  |  |  |  |  |  |  |
| 337 | Ir | 2 | 1 | P | | | | H | H | H | H | H | H | OCH3 | H | OCH3 |
|  |  |  |  | F | F | F | F |  |  |  |  |  |  |  |  |  |
|  |  |  |  | F | F | — | — |  |  |  |  |  |  |  |  |  |
|  |  |  |  | — | — | — | — |  |  |  |  |  |  |  |  |  |
| 338 | Ir | 2 | 1 | R | | | | H | H | H | OCH3 | H | H | CH3 | H | CH3 |
|  |  |  |  | H | F | H | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |
| 339 | Ir | 2 | 1 | R | | | | H | H | H | H | H | H | CH3 | H | CH3 |
|  |  |  |  | F | F | F | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |
| 340 | Ir | 2 | 1 | R | | | | H | H | H | OC6H13 | H | H | C(CH3)3 | H | C(CH3)3 |
|  |  |  |  | F | F | F | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |
| 341 | Ir | 2 | 1 | R | | | | H | H | H | N(CH3)Ph | H | H | Ph | H | Ph |
|  |  |  |  | F | F | F | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |
| 342 | Ir | 2 | 1 | R | | | | H | H | H | CH3 | H | H | CH3 | H | CH3 |
|  |  |  |  | F | F | F | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |
| 343 | Ir | 2 | 1 | S | | | | H | H | H | H | H | H | CH3 | H | CH3 |
|  |  |  |  | F | F | F | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |
| 344 | Ir | 2 | 1 | S | | | | H | H | H | OCH3 | H | H | CF3 | H | CH3 |
|  |  |  |  | F | F | F | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |
| 345 | Ir | 2 | 1 | S | | | | H | H | H | N(Ph)2 | H | H | C(CH3)3 | H | C(CH3)3 |
|  |  |  |  | F | F | F | F |  |  |  |  |  |  |  |  |  |
|  |  |  |  | — | — | — | — |  |  |  |  |  |  |  |  |  |
|  |  |  |  | — | — | — | — |  |  |  |  |  |  |  |  |  |

TABLE 24-continued

| No | M | m | n | R1 R5 | R2 R6 | R3 R7 | R4 R8 | | | | | | | | | |
|---|---|---|---|---|---|---|---|---|---|---|---|---|---|---|---|---|
| | | | | R9 | R10 | R11 | R12 | X1 | X2 | X3 | X4 | X5 | X6 | E1 | J1 | G1 |
| 346 | Ir | 2 | 1 | | T | | | H | F | H | H | H | H | CH3 | H | CH3 |
| | | | | F | H | F | H | | | | | | | | | |
| | | | | — | — | — | — | | | | | | | | | |
| 347 | Ir | 2 | 1 | | U | | | H | H | H | H | H | H | OC2H5 | H | OC2H5 |
| | | | | F | F | F | F | | | | | | | | | |
| | | | | F | F | F | F | | | | | | | | | |
| | | | | F | F | — | — | | | | | | | | | |
| 348 | Ir | 2 | 1 | | X | | | H | H | H | H | H | OCH3 | OCH3 | H | OCH3 |
| | | | | F | F | F | F | | | | | | | | | |
| | | | | F | F | F | F | | | | | | | | | |
| 349 | Ir | 2 | 1 | | C' | | | H | H | H | H | H | H | CH3 | H | CH3 |
| | | | | F | F | F | F | | | | | | | | | |
| | | | | F | F | — | — | | | | | | | | | |
| 350 | Ir | 2 | 1 | | G' | | | H | H | H | H | H | H | C(CH3)3 | H | C(CH3)3 |
| | | | | F | F | F | F | | | | | | | | | |
| | | | | — | — | — | — | | | | | | | | | |

TABLE 25

| No | M | m | n | R1 R5 | R2 R6 | R3 R7 | R4 R8 | | | | | | | | | |
|---|---|---|---|---|---|---|---|---|---|---|---|---|---|---|---|---|
| | | | | R9 | R10 | R11 | R12 | X1 | X2 | X3 | X4 | X5 | X6 | E1 | J1 | G1 |
| 351 | Ir | 2 | 1 | | J' | | | H | H | H | N(C3H7)2 | H | H | Ph | H | CH3 |
| | | | | F | F | F | F | | | | | | | | | |
| | | | | F | F | F | F | | | | | | | | | |
| | | | | — | — | — | — | | | | | | | | | |
| 352 | Ir | 2 | 1 | | M' | | | H | H | H | H | H | H | CH3 | H | CH3 |
| | | | | F | F | F | F | | | | | | | | | |
| | | | | F | F | — | — | | | | | | | | | |
| 353 | Ir | 2 | 1 | | W' | | | H | H | H | N(Ph)2 | H | H | Ph | H | Ph |
| | | | | F | F | F | F | | | | | | | | | |
| | | | | — | — | — | — | | | | | | | | | |
| 354 | Ir | 2 | 1 | | E" | | | H | H | H | H | H | H | CH3 | CH3 | CH3 |
| | | | | F | F | F | F | | | | | | | | | |
| | | | | — | — | — | — | | | | | | | | | |
| 355 | Ir | 2 | 1 | | I" | | | H | H | H | N(CH3)2 | H | H | CH3 | H | CH3 |
| | | | | F | F | F | F | | | | | | | | | |
| | | | | — | — | — | — | | | | | | | | | |
| 356 | Ir | 2 | 1 | | W" | | | H | H | H | OCH3 | H | OCH3 | C(CH3)3 | H | C(CH3)3 |
| | | | | F | F | F | F | | | | | | | | | |
| | | | | F | F | — | — | | | | | | | | | |

TABLE 25-continued

| | | | | L1 | | | | | | | | | | | L1' | | |
|---|---|---|---|---|---|---|---|---|---|---|---|---|---|---|---|---|---|
| | | | | Y1 | | | | | | | | | | | | | |
| | | | | R1 R5 | R2 R6 | R3 R7 | R4 R8 | | | | | | | | | | |
| No | M | m | n | R9 | R10 | R11 | R12 | X1 | X2 | X3 | X4 | X5 | X6 | E1 | J1 | G1 |
| 357 | Ir | 2 | 1 | X''' | | | | H | CF3 | H | H | H | H | OCH3 | H | OCH3 |
| | | | | F F — | F F — | F — — | F — — | | | | | | | | | |
| 358 | Ir | 2 | 1 | Y''' | | | | H | H | H | N(Ph)2 | H | H | CH3 | H | CH3 |
| | | | | F F — | F F — | F — — | F — — | | | | | | | | | |
| 359 | Ir | 2 | 1 | B''' | | | | H | H | H | H | H | H | CF3 | H | CF3 |
| | | | | F F — | F F — | F — — | F — — | | | | | | | | | |
| 360 | Ir | 2 | 1 | D''' | | | | H | H | H | H | N(CH3)2 | H | Ph | H | Ph |
| | | | | F F F | F F F | F F F | F F F | | | | | | | | | |
| 361 | Ir | 2 | 1 | F''' | | | | H | H | H | OCH3 | H | H | CH3 | H | CH3 |
| | | | | F F F | F F F | F F — | F F — | | | | | | | | | |
| 362 | Ir | 2 | 1 | H''' | | | | H | H | H | OC4H9 | H | H | C(CH3)3 | H | C(CH3)3 |
| | | | | F F F | F F F | F F — | F F — | | | | | | | | | |
| 363 | Ir | 2 | 1 | U''' | | | | H | H | H | OC2H5 | H | H | OCH3 | H | OCH3 |
| | | | | F F — | F F — | F F — | F F — | | | | | | | | | |
| 364 | Ir | 2 | 1 | W''' | | | | H | H | H | H | H | H | CH3 | H | CH3 |
| | | | | F F — | F F — | F F — | F F — | | | | | | | | | |
| 365 | Ir | 2 | 1 | A'''' | | | | H | H | H | N(CH3)2 | H | H | C(CH3)3 | H | C(CH3)3 |
| | | | | F F — | F F — | F F — | F F — | | | | | | | | | |

Next, the light-emitting device of the present invention will be described.

The light-emitting device of the present invention is an electroluminescent device in which an organic compound layer containing the metal complex compound of the present invention is interposed between two opposing electrodes and a voltage is applied between the electrodes to emit light.

An organic compound layer containing the metal complex compound of the present invention can be formed by vacuum vapor deposition, a casting method, a coating method, a spin coating method, an ink jet method, or the like.

Figure 1B:
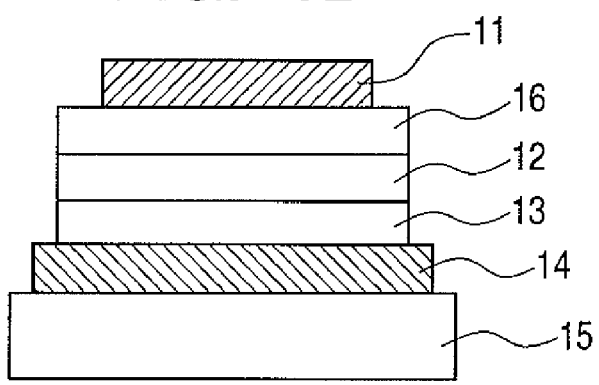
Figure 1C:
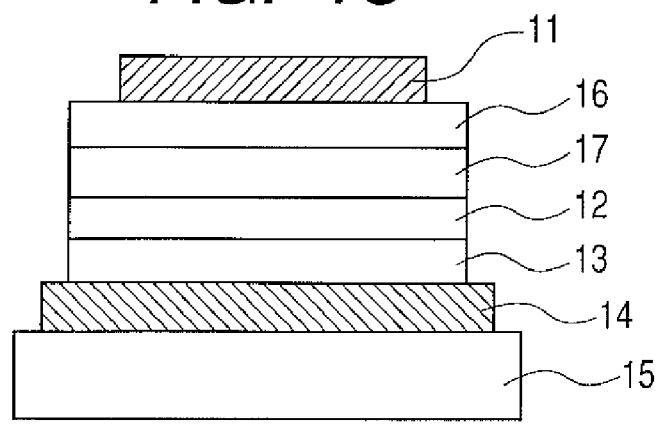

Basic configurations of the device of the present invention are illustrated in FIGS. 1A, 1B and 1C.

First, description of the reference numerals will be made. Reference numeral 11 denotes a metal electrode, 12 denotes a light-emitting layer, 13 denotes a hole-transporting layer, 14 denotes a transparent electrode, 15 denotes a transparent substrate, 16 denotes an electron-transporting layer, and 17 is an exciton diffusion prevention layer.

As shown in FIGS. 1A, 1B and 1C, in the organic EL device of the present invention, on a transparent substrate 15, there are formed a transparent electrode 14 having a thickness of 50 nm to 200 nm, a plurality of organic compound layers, and a metal electrode 11 for interposing the plurality of organic compound layers between the transparent electrode 14 and the metal electrode 11.

FIG. 1A shows an example in which the organic compound layers include a light-emitting layer 12 and a hole-transporting layer 13. ITO having a large work function is used for the transparent electrode 14, so that holes can be easily injected from the transparent electrode 14 into the hole-transporting layer 13. A metal material having a small work function such as aluminum, magnesium, or an alloy using any one of them is used for the metal electrode 11, so that electrons can be easily injected to the organic compound layers.

For the light-emitting layer 12, the metal complex compound of the present invention is preferably used, while for the hole-transporting layer 13, there can suitably be used an electron-donative material such as a triphenyldiamine (TPD) derivative typified by α-NPD shown below.

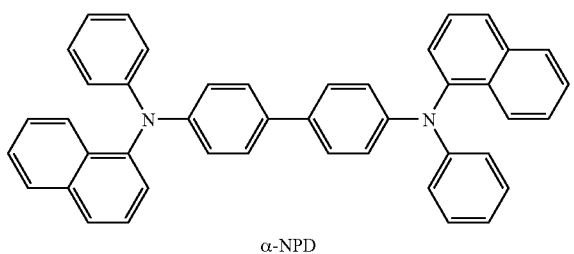

α-NPD

The device having the structure as described above exhibits electrical rectifying property. When an electric field is applied such that the metal electrode 11 becomes a cathode and the transparent electrode 14 becomes an anode, electrons are injected from the metal electrode 11 into the light-emitting layer 12, while holes are injected from the transparent electrode 14 to the light-emitting layer 12.

The injected holes and electrons are recombined in the light-emitting layer 12 to generate excitons, thereby causing light emission. At this time, the hole-transporting layer 13 serves as an electron-blocking layer. As a result, the recombination efficiency at an interface between the light-emitting layer 12 and the hole-transporting layer 13 increases to thereby increase the emission efficiency.

Further, in FIG. 1B, an electron-transporting layer 16 is provided between the metal electrode 11 and the light-emitting layer 12 shown in FIG. 1A. The light-emitting function and electron/hole transporting functions are separated from each other to establish a more effective carrier blocking structure, whereby the emission efficiency is increased. For the electron-transporting layer 16, for example, an oxadiazole derivative can be used.

Further, as shown in FIG. 1C, a four-layer structure can preferably be adopted which includes the hole-transporting layer 13, the light-emitting layer 12, an exciton diffusion prevention layer 17, and the electron-transporting layer 16 in the stated order from the side of the transparent electrode 14 as the anode to the side of the metal electrode 11 as the cathode.

The optical EL device having high efficiency according to the present invention can be applied to products which require energy saving or high luminance. Examples of such applications include a display apparatus, a light source of a printer, an illumination apparatus, and a backlight for a liquid crystal display apparatus. The application to the display apparatus can provide a lightweight and energy-saving flat panel display with a high level of visibility. In addition, for the light source of a printer, a laser light source of a laser beam printer which is widely used at present can be replaced with the organic EL device of the present invention. An image can be formed by disposing devices which can be addressed independently from one another on an array and by performing a desired exposure with respect to a photosensitive drum by use thereof. The use of the organic EL device of the present invention can significantly reduce the size of an apparatus. The organic EL device of the present invention is expected to provide an energy-saving effect on the illumination apparatus and the backlight.

The display apparatus of the present invention includes the electroluminescent device of the present invention and a unit for driving the electroluminescent device.

The application to the display apparatus includes application to a display of a system in which the organic EL devices are driven using an active-matrix TFT drive circuit.

Hereinafter, an example in which an active matrix substrate is used in the device of the present invention will be described with reference to FIGS. 2, 3 and 4.

Figure 2:
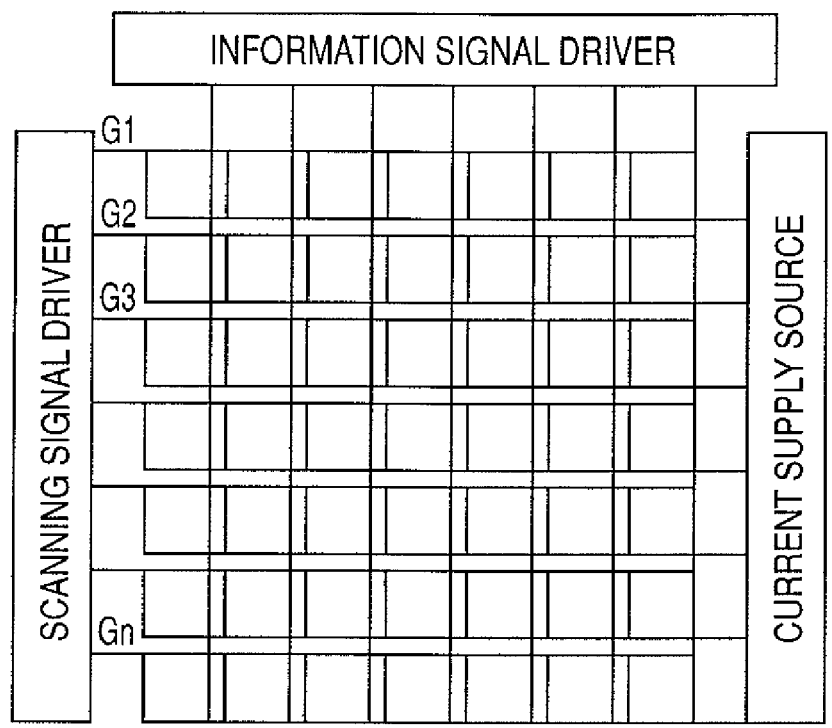
FIG. 2 is a diagram schematically illustrating an example of the constitution of a panel provided with an EL device and a driving unit.
Figure 3:
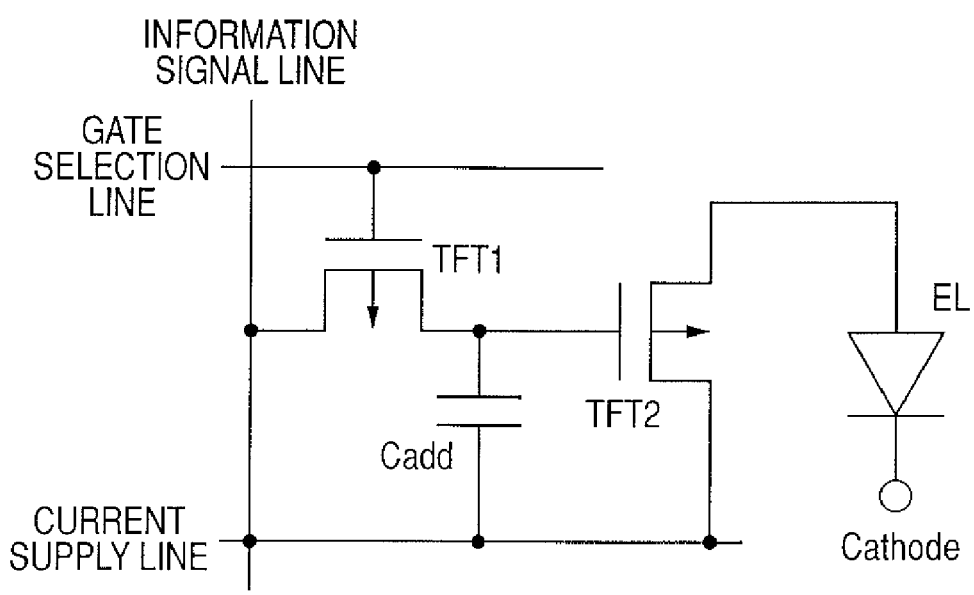
FIG. 3 is a diagram illustrating an example of a pixel circuit.

FIG. 2 schematically shows an example of the configuration of a panel provided with an EL device and a drive unit. A scanning signal driver, an information signal driver, and a current supply source are disposed on the panel, and are connected to gate selection lines, information signal lines, and current supply lines, respectively. A pixel circuit shown in FIG. 3 is disposed at the point of intersection of a gate selection line and an information signal line. The scanning signal driver selects gate selection lines G1, G2, G3, . . . , Gn sequentially, and an image signal is applied from the information signal driver in synchronization with the selection.

Next, the operation of the pixel circuit will be described. When a selection signal is applied to the gate selection line in the pixel circuit, a TFT 1 is turned on, an image signal is supplied to a Cadd, and the gate potential of a TFT 2 is determined. A current is supplied from the current supply line to the EL device in accordance with the gate potential of the TFT 2. Since the gate potential of the TFT 2 is kept in the Cadd until the TFT 1 is subjected to the subsequent scanning selection, the current continues to flow in the EL device by the subsequent scanning. As a result, the EL device can be caused to emit light at all times during one frame period.

FIG. 4 is a schematic view illustrating an example of a sectional structure of a TFT substrate to be used in the present invention. A p-Si layer is provided on a glass substrate, and each of channel, drain, and source regions is doped with a necessary impurity. A gate electrode is provided on the layer with a gate insulating film interposed between the electrode and the layer, and a drain electrode to be connected to the drain region and a source electrode to be connected to the source region are formed. An insulating layer and an ITO electrode as a pixel electrode are stacked on the electrodes, and the ITO electrode and the drain electrode are connected to each other through a contact hole.

The application of the present invention is not particularly limited to a switching device, and the present invention is easily applicable to, for example, a single crystal silicon substrate, a MIM device, or an a-Si type device.

An organic EL display panel can be obtained by sequentially stacking one or more organic EL layers and a cathode layer on the ITO electrode. An image with good image quality can be stably displayed for a long period of time by driving the display panel using the organic compound of the present invention.

EXAMPLES

Hereinafter, the present invention will be described specifically by way of examples. However, the present invention is not limited to those examples.

Example 1

Synthesis of Exemplified Compound Nos. 339 and 76

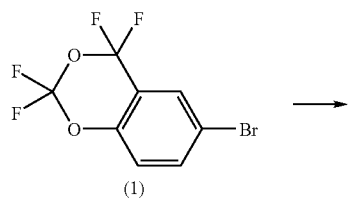

24.0 g (83.6 mmole) of 6-bromo-2,2,4,4-tetrafluoro-1,3-benzodioxane (1) manufactured by Apollo and 240 ml of diethyl ether were placed in a 1-L three-necked flask. Under argon flow, the solution was cooled to −78° C., and 34.4 ml (2.67 mol/L, 92.0 mmole) of a solution of n-butyllithium in hexane was added to the solution over 4 minutes. After the completion of the addition, the mixture was stirred for 3 minutes at the same temperature, and 17.1 g (92.0 mmole) of 2-isopropoxy-4,4,5,5-tetramethyl-1,3,2-dioxaborolane was added to the mixture at ones. The temperature of the mixture was raised to 0° C. over 1 hour, and then 300 ml of a 10% aqueous solution of ammonium chloride was added to the mixture. The separated organic layer was washed with saturated brine and dried with anhydrous magnesium sulfate, and the solvent was evaporated to dryness under reduced pressure. The residue was purified by means of silica gel column chromatography (eluent: chloroform/hexane mixed solvent) and recrystallized from hexane to give 18.5 g of a colorless crystal of a compound (2) (66.2% yield).

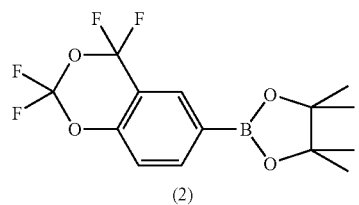

5.00 g (15.0 mmole) of the compound (2), 3.10 g (18.0 mmole) of 2-bromo-4-methylpyridine, 25 ml of toluene, 12.5 ml of ethanol, and 25 ml of a 2-M aqueous solution of sodium carbonate were placed in a 200-ml three-necked flask. 0.87 g (0.75 mmole) of tetrakis-(triphenylphosphine)palladium(0) was added to the mixture with stirring under nitrogen flow at room temperature. After that, the mixture was refluxed with stirring under nitrogen flow for 3 hours. After the completion of the reaction, the reaction product was cooled and extracted with cold water and toluene. The organic layer was washed with brine and dried with magnesium sulfate, and the solvent was evaporated to dryness under reduced pressure. The residue was purified by means of silica gel column chromatography (eluent: chloroform) to give 3.30 g of 2-(2,2,4,4-tetrafluoro-1,3-benzodioxan-6-yl)pyridine (3) (73.7% yield).

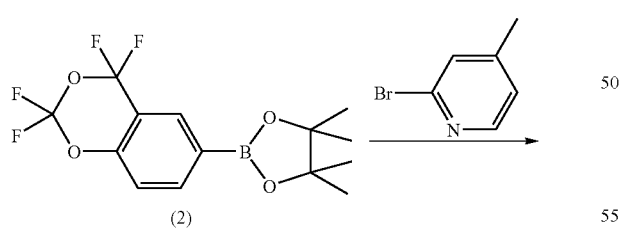

The followings were placed in a 200-ml three-necked flask. 621 mg (1.65 mmole) of iridium (III) chloride trihydrate, 1,035 mg (3.46 mmole) of 2-(2,2,4,4-tetrafluoro-1,3-benzodioxane-6-yl)pyridine (3), 45 ml of ethoxyethanol, and 15 ml of water.

The mixture was stirred under nitrogen flow at room temperature for 30 minutes, and was then stirred with heating at 90° C. for 17 hours. The reaction product was cooled to room temperature, and the precipitate was filtered off and washed with water and then with ethanol. The resultant was dried under reduced pressure at 120° C. to give 693 mg of a pale yellow powder of tetrakis[2-(2,2,4,4-tetrafluoro-1,3-henzo-dioxan-6-yl)pyridine-$C^7$,N](µ-dichloro)diiridium(III) (4) (51.0% yield).

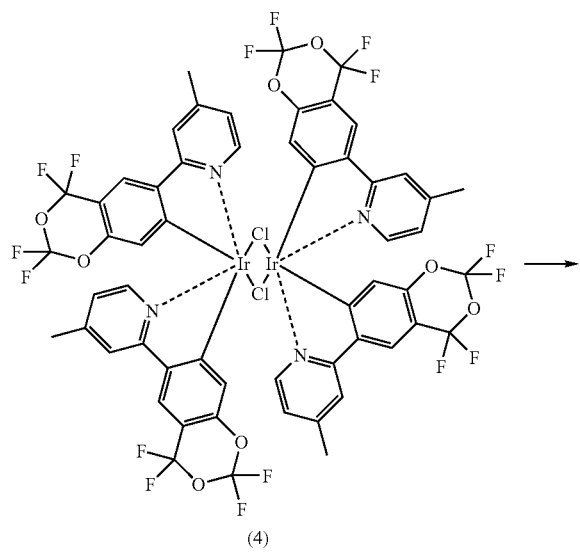

(4)

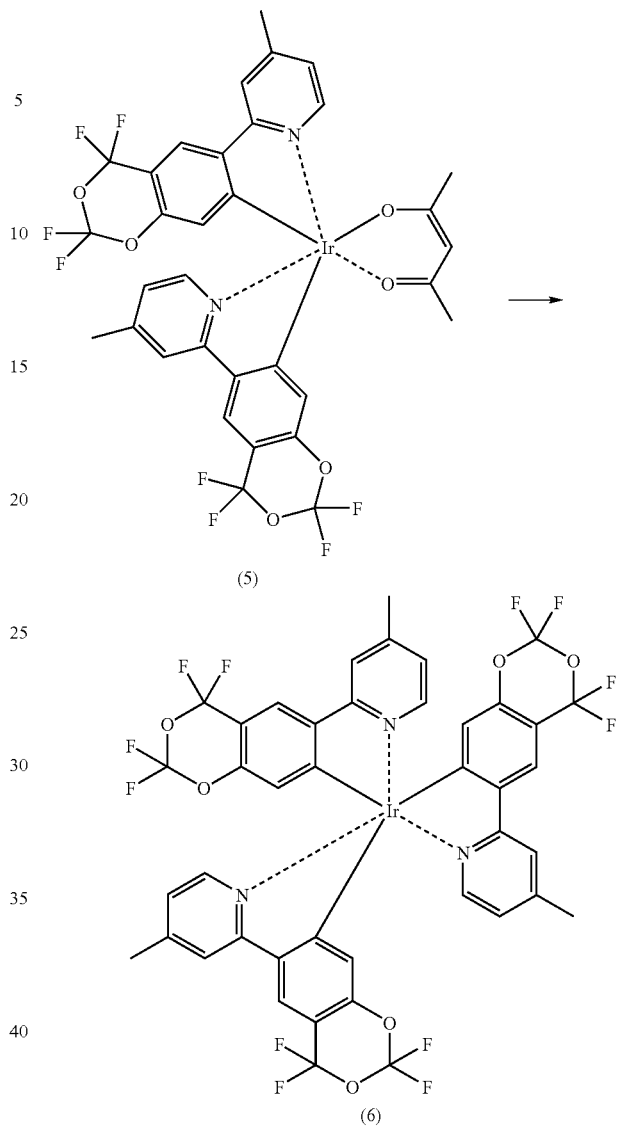

(5)

(5)

(6)

The followings were placed in a 100-ml three-necked flask.

25 ml of ethoxyethanol, 693 mg (0.42 mmole) of tetrakis[2-(2,2,4,4-tetrafluoro-1,3-benzodioxane-6-yl)pyridine-$C^7$,N] (μ-dichloro)diiridium (III) (4), 132 mg (1.32 mmole) of acetylacetone, and 356 mg (3.36 mmole) of sodium carbonate.

The mixture was stirred under nitrogen flow at room temperature for 1 hour, and was then refluxed with stirring for 15 hours. The reaction product was cooled with ice, and the precipitate was filtered off and washed with water and then with ethanol. The resultant was dried under reduced pressure at room temperature to give 486 mg of a pale yellow powder of bis[2-(2,2,4,4-tetrafluoro-1,3-benzodioxan-6-yl)pyridine-$C^7$,N](acetylacetonato)iridium(III) (5) (Exemplified Compound No. 339) (65.1% yield). The emission spectrum of a solution of the compound in toluene had a λmax of 479 nm. Further, 888.1 as M+ of the compound was confirmed by means of Matrix Assisted Laser Desorption/Ionization-Time of Flight Mass Spectrometry (MALDI-TOF MS).

The followings were placed in a 100-ml three-necked flask.

511 mg (1.71 mmole) of 2-(2,2,4,4-tetrafluoro-1,3-benzodioxane-6-yl)pyridine, 486 mg (0.57 mmole) of bis[2-(2,2,4,4-tetrafluoro-1,3-benzodioxane-6-yl)pyridine-$C^7$,N] (acetylacetnate)iridium (III) (5), and 20 ml of glycerol.

The mixture was heated with stirring under nitrogen flow at around 220° C. for 8 hours. The reaction product was cooled to room temperature and poured into 100 ml of distilled water, and the precipitate was filtered off and washed with water. The precipitate was dissolved in chloroform and dried with magnesium sulfate, and the solvent was evaporated to dryness under reduced pressure. The residue was purified by means of silica gel column chromatography (eluent: chloroform/hexane mixed solvent) and recrystallized from chloroform/hexane mixed solvent to give 212 mg of a pale yellow powder of tris[2-(2,2,4,4-tetrafluoro-1,3-benzodioxan-6-yl)pyridine-$C^7$,N]iridium(III) (6) (Exemplified Compound No. 76) (35.6% yield). The emission spectrum of a solution of the compound in toluene had a λmax of 467 nm. Further, 1087.1 as M+ of the compound was confirmed by means of Matrix Assisted Laser Desorption/Ionization-Time of Flight Mass Spectrometry (MALDI-TOF MS).

Example 2

Synthesis of Exemplified Compound Nos. 343 and 88

By following the same procedure as in Example 1 with the exception that 6-bromo-2,2,3,3-tetrafluoro-1,4-benzodioxane manufactured by Oakwood is used instead of 6-bromo-2,2,4,4-tetrafluoro-1,3-benzodioxane (1), the following compounds can be sequentially synthesized.

Tetrakis[2-(2,2,3,3-tetrafluoro-1,4-benzodioxan-6-yl)pyridine-$C^7$,N] (μ-dichloro)diiridium(III) instead of the compound (4)

Bis[2-(2,2,3,3-tetrafluoro-1,4-benzodioxan-6-yl)pyridine-$C^7$,N] (acetylacetonato) iridium(III) (Exemplified Compound No. 343) instead of the compound (5)

Tris[2-(2,2,3,3-tetrafluoro-1,4-benzodioxan-6-yl)pyridine-$C^7$,N]iridium(III) (Exemplified Compound No. 88) instead of the compound (6)

Example 3

Synthesis of Exemplified Compound Nos. 316 and 24

By following the same procedure as in Example 1 with the exception that 5-bromo-2,2-difluorobenzodioxol manufactured by Oakwood is used instead of 6-bromo-2,2,4,4-tetrafluoro-1,3-benzodioxane (1), the following compounds can be sequentially synthesized.

Tetrakis[2-(2,2-difluorobenzodioxol-5-yl)pyridine-$C^7$,N](μ-dichloro)diiridium(III) instead of the compound (4)

Bis[2-(2,2-difluorobenzodioxol-5-yl)pyridine-$C^7$,N] (acetylacetonato)iridium(III) (Exemplified Compound No. 316) instead of the compound (5)

Tris[2-(2,2-difluorobenzodioxol-5-yl)pyridine-$C^7$,N]iridium(III) (Exemplified Compound No. 24) instead of the compound (6)

Example 4

A device having the configuration with three organic compound layers shown in FIG. 1B was produced.

ITO (transparent electrode 14) having a thickness of 100 nm was patterned onto a glass substrate (transparent substrate 15) so as to have an opposing electrode area of 3 mm$^2$. The following organic layers and electrode layers were sequentially formed on the ITO substrate through vacuum vapor deposition using resistive heating in a vacuum chamber at $10^{-4}$ Pa to produce a device.

Hole-transporting layer 13 (40 nm): α-NPD
Light-emitting layer 12 (30 nm): MCP:Exemplified Compound No. 76 (weight ratio 95:5)
Electron-transporting layer 16 (30 nm): TPBI
Metal Electrode 11-1 (10 nm): LiF
Metal Electrode 11-2 (100 nm): Al The structural formulae of MCP and TPBI are shown below.

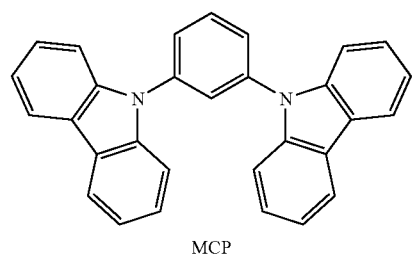

MCP

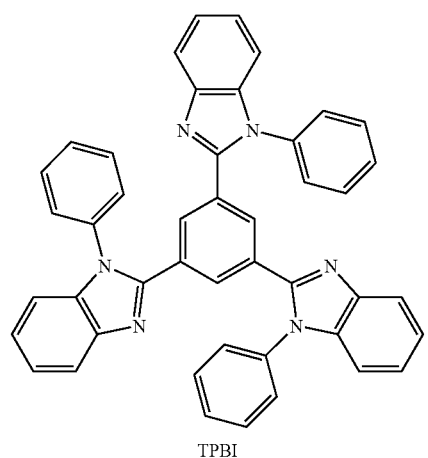

TPBI

The device characteristics were evaluated by applying an electric field to the thus produced device in such a manner that the ITO side served as an anode and the Al side served as a cathode. When the device was energized under such conditions that the initial luminance became 100 cd/m$^2$, stable blue light emission was attained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-320083, filed Nov. 28, 2006, which is hereby incorporated by reference in its entirety.

What is claimed is:

1. An electroluminescent device in which a light-emitting layer is disposed between a pair of opposing electrodes and a voltage is applied between the electrodes to emit light, wherein the light-emitting layer comprises:
a metal coordination compound represented by the following general formula:

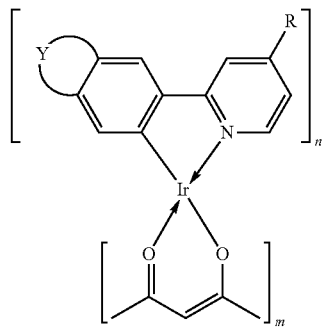

wherein Y forms a 5- or 6-membered ring group, provided that when Y forms a 5-membered ring group, Y is —O—CF$_2$—O—, and when Y forms a 6-membered ring group, Y is —O—CF$_2$—O—CF$_2$—, —O—CF$_2$—CF$_2$—O—, or —CF$_2$—O—CF$_2$—O—;
n is an integer of 2 or 3 and m is an integer of 0 or 1 provided that n+m=3; and
R is a hydrogen atom or methyl group, and
a compound represented by the following structural formula:

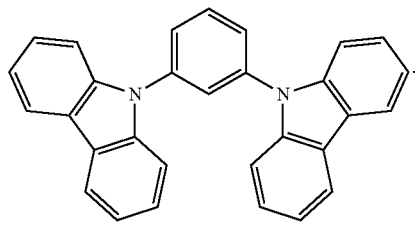

2. The electroluminescent device according to claim 1, wherein the metal coordination compound is represented by the following structural formula:

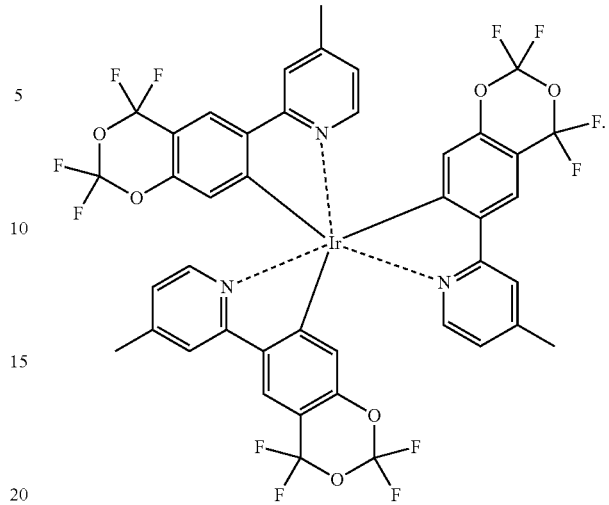

3. A display apparatus comprising the electroluminescent device set forth in claim 1 and a unit for driving the electroluminescent device.

4. The display apparatus according to claim 3, wherein the unit for driving the electroluminescent device comprises a scanning signal driver and an information signal driver.

5. The display apparatus according to claim 3, wherein the unit for driving the electroluminescent device comprises a switching device.

6. The display apparatus according to claim 5, wherein the switching device comprises a TFT.

7. A light source of a printer comprising the electroluminescent device set forth in claim 1.

8. An illumination apparatus comprising the electroluminescent device set forth in claim 1.

9. A backlight for a liquid crystal display apparatus comprising the electroluminescent device set forth in claim 1.

* * * * *